(12) United States Patent
MacKay

(10) Patent No.: US 8,071,096 B2
(45) Date of Patent: Dec. 6, 2011

(54) ANTI-C5AR ANTIBODIES AND USES THEREOF

(75) Inventor: Charles Reay MacKay, Vaucluse (AU)

(73) Assignee: G2 Therapies Ltd, Darlinghurst (AU)

( * ) Notice: Subject to any disclaimer, the term of this patent is extended or adjusted under 35 U.S.C. 154(b) by 1571 days.

(21) Appl. No.: 10/502,145

(22) PCT Filed: Jan. 24, 2003

(86) PCT No.: PCT/AU03/00084
§ 371 (c)(1), (2), (4) Date: May 5, 2005

(87) PCT Pub. No.: WO03/062278
PCT Pub. Date: Jul. 31, 2003

(65) Prior Publication Data
US 2005/0244406 A1  Nov. 3, 2005

Related U.S. Application Data

(60) Provisional application No. 60/350,961, filed on Jan. 25, 2002.

(51) Int. Cl.
*A61K 39/395* (2006.01)
*C07K 16/28* (2006.01)
*C12N 15/13* (2006.01)
*G01N 33/53* (2006.01)

(52) U.S. Cl. ............... 424/144.1; 424/130.1; 424/133.1; 424/141.1; 424/143.1; 424/152.1; 424/172.1; 424/178.1; 424/183.1; 424/9.1; 435/7.1; 435/334; 530/387.1; 530/387.3; 530/388.1; 530/388.2; 530/388.22; 530/391.3; 530/391.7; 536/23.1; 536/23.5; 536/23.53

(58) Field of Classification Search .................. None
See application file for complete search history.

(56) References Cited

U.S. PATENT DOCUMENTS 5,480,974 A * 1/1996 Morgan et al. ............. 530/387.9
5,861,272 A    1/1999 Li et al.

FOREIGN PATENT DOCUMENTS

| EP | 0 377 489 | 7/1990 |
| JP | 08109200 | 4/1996 |
| WO | WO 95/00164 | 1/1995 |
| WO | WO 96/39511 | 12/1996 |
| WO | WO 98/33908 | 7/1998 |
| WO | WO 02/38767 | 5/2002 |

OTHER PUBLICATIONS

Rudikoff, et al. Proc Natl Acad Sci USA [1982] 79:1979-1983.*
MacCallum, RM et al. J. Mol. Biol. [1996] 262:732-745.*
Casset, F et al. Biochem. Biophys. Res. Comm. [2003] 307:198-205.*
Wu, H et al. J. Mol. Biol. [1999] 294:151-162.*
FitzGerald, DJP. Meth. Enzymol [1987] 151:139-145.*
Colman, Research in Immunology 145: 33-36, 1994.*
Kussie et al., J. Immunol. 152: 146-152, 1994.*
Chen et al., EMBO J., 14: 2784-2794, 1995.*
Crass et al., J. Biol. Chem 274: 8367-8370, 1999.*
Pease et al. (Eur. J. Immunol 24: 211-215, 1994.*
Elsner, et al., "C3a activates the respiratory burst in human polymorphonuclear neutrophilic leukocytes via pertussis toxin-sensitive g-proteins", Blood, (1994), vol. 83, No. 11, pp. 33224-33331.
Farkas et al., "C5a receptor expression by TGW neuroblastoma cells", NeuroReport (1999), vol. 10, No. 14, pp. 3021-3025.
Fayyazi et al., "The C5a receptor is expressed in normal renal proximal tubular but not in normal pulmonary or hepatic epithelial cells", Immunology, (2000), vol. 99, No. 1, pp. 38-45.
Jagels, et al., "Proteolytic inactivation of the leukocyte C5a receptor by proteinases derived from *Porphyromonas gingivalis*", Infection and Immunity, (1996), vol. 64, No. 6, pp. 1984-1991.
Oppermann, et al., "Probing the human receptor for C5a anaphylatoxin with site-directed antibodies", The Journal of Immunology, (1993) vol. 151, No. 7, pp. 3785-3794.
Schlaf, et al., "Differential expression of the C5a receptor on the main cell types of rat liver as demonstrated with a novel monoclonal antibody and by C5a anaphylatoxin-induced $Ca^{2+}$ release", Laboratory Investigation, (1999) vol. 79, No. 10, pp. 1287-1297.
Sayah, et al., "Expression of cytokines by human astrocytomas following stimulation by C3a anaphylatorxins: specific increase in interleukin-6 mRNA expression", Journal of Neurochemistry (1999), col. 72, No. 6, pp. 2426-2436.
Watanabe, et al., "Analysis of C5a receptor by monoclonal antibody", Journal of Immunological Methods, (1995), vol. 185, No. 1, pp. 19-29.
Charlton R. et al. "The Expression of C5A Receptor (C5AR) (CD88) Is Associated with the Progression of Inflammation in Human Disease". Journal of Pathology, Chichester, Sussex, GB, vol. 187, No. suppl. 1999, p. 36A.
Monk, et al., Mutation of Glutamate 199 of the Human C5a Receptor Defines a Binding Site for Ligand Distinct from the Receptor N Terminus, The American Society for Biochemistry and Molecular Biology, Inc., vol. 270, No. 28, Issue of Jul. 14, pp. 16625-16629, 1995.
Cain et al., Mapping the Ligand-Binding Site on the C5a Receptor: Arginine74 of C5a Contacts Aspartate282 of the C5a Receptor. Biochemistry 2001;40:14047-52.
Cain et al., Modulation of ligand selectivity by mutation of the first extracellular loop of the human C5a receptor. Biochem. Pharm. 2001;61:1571-9.
Crass et al., Receptor Activation by Human C5a des Arg74 but Not Intact C5a Is Dependent on an Interaction between Glu199 of the Receptor and Lys68 of the Ligand. Biochemistry 1999;38:9712-17.

(Continued)

*Primary Examiner* — Phillip Gambel
(74) *Attorney, Agent, or Firm* — Carol L. Francis; Bozicevic, Field & Francis LLP

(57) ABSTRACT

The present invention relates to antibodies which bind to C5aR and which are useful in diagnostic and therapeutic methods. The antibodies of the present invention are reactive with an extracellular loop of C5aR other than the N-terminal domain and are capable of substantially reducing or inhibiting the binding of C5a to C5aR and functional consequences of neutrophil chemoattractant receptor activation.

67 Claims, 15 Drawing Sheets

OTHER PUBLICATIONS

Demartino et al., Arginine 206 of the C5a Receptor Is Critical for Ligand Recognition and Receptor Activation by C-terminal Hexapeptide Analogs. J. Biol. Chem. 1995;270(27):15966-9.

Gerber et al., An Activation Switch in the Ligand Binding Pocket of the C5a Receptor. J. Biol. Chem. 2001;276:3394-3400.

Lee et al., Human C5aR knock-in mice facilitate the production and assessment of anti-inflammatory monoclonal antibodies. Nature Biotechnology 2006;24(10):1279-84.

Lee et al., 2006, "Human C5aR knock-in mice facilitate the production and assessment of anti-inflammatory monoclonal antibodies," Nature Biotechnology, 24(10):1279-1284.

Extended European Search Report for European Application No. 10009060.4, dated Jul. 29, 2011.

Raffetseder, et al. (1996) "Site-Directed Mutagenesis of Conserved Charged Residues in the Helical Region of the Human C5a Receptor. Arg2O6 Determines High-Affinity Binding Sites of C5a Receptor" Eur. J. Biochem. 235 (1-2):82-90.

Rothermel, et al. (2000) "Analysis of the Tissue Distribution of the Rat C5a Receptor and Inhibition of C5a-Mediated Effects through the Use of Two MoAbs" Scand. J. Immunol. 52(4):401-410.

* cited by examiner

Anti-C5aR MAb variable light chain DNA sequences

```
              10         20         30         40         50
7F3  Vk   GATGTTGTGATGACCCAATCTCCACTCTCCCTGCCTGTCAGTCTTGGAAA
6c12 Vk   GATGTTGTGATGACCCAAATTCCACTCTCCCTGCCTGTCAGTCTTGGAGA
12d4 Vk   GATGTTGTGATGACCCAAACTCCACTCTCCCTGCCTGTCAGTCTTGGAGA
          ****************  ************************** *

60         70         80         90        100
7F3  Vk   TCAAGCCTCCATCTCTTGCAGATCTAGTCAGAGCCTTGTACACAGTAATG
6c12 Vk   TCAAACCTCCATCTCTTGCAGATCTAGTCAGAGCCTTATACACAGTAATG
12d4 Vk   TCAAGCCTCCATCTCTTGTAGATCTAGTCAGAGCCTTGTACACAGTAGTG
          ****  ************ ***************** ********* **

110        120        130        140        150
7F3  Vk   GAAACACCTATTTACATTGGTACCTGCAGAAGCCAGGCCAGTCTCCAAAG
6c12 Vk   GAAACACCTATTTACATTGGTACCTGCAGAAGCCAGGCCAGTCTCCAAAG
12d4 Vk   GAAACACCTATTTACATTGGTACCTGCAGAAGCCAGGCCAGTCTCCAAAG
          **************************************************

160        170        180        190        200
7F3  Vk   CTCCTGATCTACAAAGTTTCCAACCGATTTTCTGGGGTCCCAGACAGGTT
6c12 Vk   CTCCTGATCTACAAAGTTTCCAACCGATTTTCTGGGGTCCCAGACAGGTT
12d4 Vk   CTCCTGATCTACAAAGTCTCCAACCGATTTTCTGGGGTCCCAGACAGGTT
          ***************** ********************************

210        220        230        240        250
7F3  Vk   CAGTGGCAGTGGATCAGGGACAGATTTCTCACTCAAGATCAGCAGAGTGG
6c12 Vk   CAGTGGCAGTGGATCAGGGACAGATTTCACACTCAAGATCAGCAGAGTGG
12d4 Vk   CAGTGGCAGTGGATCAGGGACACATTTCACACTCAAGATCAGCAGAGTGG
          ********************* ***** *********************

260        270        280        290        300
7F3  Vk   AGGCTGAGGATCTGGGAGTTTATTTCTGCTCTCAAAGTACACTTGTTCCG
6c12 Vk   AGGCTGAGGATATGGGAGTTTATTTCTGCTCTCAAAGTACACATGTTCCT
12d4 Vk   AGGCTGAGGATCTGGGAATTTATTTCTGCTCTCAAAGTACACTTGTTCCT
          ***********  ***** *********************** ******

310        320        330
7F3  Vk   CTCACGTTCGGTGCTGGGACCAAGCTGGAACTGAAA
6c12 Vk   CCGACGTTCGGTGGAGGCACCAAGCTGGAAATCAAA
12d4 Vk   CCGACGTTCGGTGGAGGCACCAAGCTGGAAATCAAA
          * ********* ** ************ * ***
```

Figure 11

Anti-C5aR MAb variable heavy chain DNA sequences

```
                      10        20        30        40        50
7F3  Vh    CAGGTTCAGCTGCAGCAGTCTGGACCTGAGCTGGTGAAGCCTGGGGCCTC
6c12 Vh    CAGGTTCAGCTGCAGCAGTCTGGACCTGAGGTGGTGAAGCCTGGGGCCTC
12d4 Vh    CAGGTGCAGCTGAAGGAGTCAGGACCTGGCCTGGTGGCGCCCTCACAGAG
           ***** ****** ** **** *******     *****  ***

60        70        80        90        100
7F3  Vh    AGTGAAGATTTCCTGCAAGGCTTCTGGCTACGCATTCAGTAACTCCTGGA
6c12 Vh    AGTGAAGATTTCCTGCAAGGCTTCTGGCTACGCATTCAGTAGGTCCTGGA
12d4 Vh    CCTGTCCATCACATGCACTGTCTCTGGGTTCTCATTAACCAGCTATGGTG
            **    **  *  ****  *      *****   *  **** *  *  *

110       120       130       140       150
7F3  Vh    TGAACTGGGTGAAGCAGAGGCCTGGAAAGGGTCTTGAGTGGATTGGACGG
6c12 Vh    TGAACTGGGTGAAGCAGAGGCCTGGAAAGGGTCTTGAGTGGATTGGACGG
12d4 Vh    TAGACTGGGTTCGCCAGTCTCCAGGAAAGGGTCTGGAGTGGCTGGGAGTA
           * *******   ***      ** *********** ****** *  ***

160       170       180       190       200
7F3  Vh    ATTTATCCTGGAGATGGAGATACTAAGTACAATGGGAAGTTCAAGGGCAA
6c12 Vh    ATTGATGCTGGAGATGGAGATACTAAATACAATGGGAAGTTCAAGGGCAA
12d4 Vh    ATATG---GGGTGTTGGAAGCACAAATTATAATTCAGCTCTCAAATCCAG
           **      **  *  **  **  *  *** ***          ****  **

210       220       230       240       250
7F3  Vh    GGCCACACTGACTGCAGACAAATCCTCCAGCACAGCCTACATGCAACTCA
6c12 Vh    GGCCACACTGACTGCAGACAAATCCTCCAGCACAGCCTACATGCAACTCA
12d4 Vh    ACTGAGCATCAGCAAGGACAACTCCAAGAGCCAAGTTTTCTTAAAAATGA
             *  * *        *****  ***   ***  **  * *  **  *

260       270       280       290       300
7F3  Vh    GCAGCCTGACATCTGAGGACTCTGCGGTCTATTTCTGTGCAAGATTCCTA
6c12 Vh    GCAGCCTGACATCTGAGGACTCTGCGGTCTACTTCTGTGCAAGCCTTCTC
12d4 Vh    ACAGTCTGCAAACTGATGACGCAGCCATGTACTACTGTGCCAGCCACT--
           *** ***   * **** ***   *  *  **   * ****** **

310       320       330       340       350
7F3  Vh    CTTATTAGTACGGTAACAGCCGTTGACTACTGGGGCCAAGGCACCACTCT
6c12 Vh    ATTACTACGGTAGTGGGAGCTATGGACTACTGGGGTCAAGGAACCTCAGT
12d4 Vh    ATGGTTACGACGGTCTGGGGT-TTGCTTACTGGGGCCAAGGGACTCTGGT
            *   **    **   **  *     ******* *****  ** *    *

360
7F3  Vh    CACAGTCTCCTCA
6c12 Vh    CACCGTCTCCTCA
12d4 Vh    CACTGTCTCTGTA
           *** *****    *
```

Figure 12

Anti-C5aR MAb variable light chain protein sequences

```
               FR1                      CDR1           FR2
        10         20            30              40         50
7F3  Vk  DVVMTQSPLSLPVSLGNQASISC  RSSQSLVHSNGNTYLH  WYLQKPGQSPK
6c12 Vk  DVVMTQIPLSLPVSLGDQTSISC  RSSQSLIHSNGNTYLH  WYLQKPGQSPK
12d4 Vk  DVVMTQTPLSLPVSLGDQASISC  RSSQSLVHSSGNTYLH  WYLQKPGQSPK
         ****** ********* *.****  ******.** ******  **********

CDR2              FR3                        CDR3
            60          70        80        90             100
7F3  Vk  LLIY  KVSNRFS  GVPDRFSGSGSGTDFSLKISRVEAEDLGVYFC  SQSTLVP
6c12 Vk  LLIY  KVSNRFS  GVPDRFSGSGSGTDFTLKISRVEAEDMGVYFC  SQSTHVP
12d4 Vk  LLIY  KVSNRFS  GVPDRFSGSGSGTHFTLKISRVEAEDLGIYFC  SQSTLVP
         ****  *******  ************* *.*********.*.***  **** **

FR4
              110
7F3  Vk  LT  FGAGTKLELK
6c12 Vk  PT  FGGGTKLEIK
12d4 Vk  PT  FGGGTKLEIK
          *  ** *****.*
```

Figure 13

Anti-C5aR MAb variable heavy chain protein sequences

```
              FR1                            CDR1    FR2
         10        20        30                      40              50
7F3 Vh   QVQLQQSGPELVKPGASVKISCKASGYAFS     NSWMN   WVKQRPGKGLEWIG   R
6c12 Vh  QVQLQQSGPEVVKPGASVKISCKASGYAFS     RSWMN   WVKQRPGKGLEWIG   R
12d4 Vh  QVQLKESGPGLVAPSQSLSITCTVSGFSLT     SYGVD   WVRQSPGKGLEWLG   V
         ****..***.*  *  *. *.*  **..  .           **.* *******.*

CDR2                    FR3
              60        70        80        90        100
7F3 Vh   IYPGDGDTKYNGKFKG   KATLTADKSSSTAYMQLSSLTSEDSAVYFCAR   FL
6c12 Vh  IDAGDGDTKYNGKFKG   KATLTADKSSSTAYMQLSSLTSEDSAVYFCAS   LL
12d4 Vh  IW-GVGSTNYNSALKS   RLSISKDNSKSQVFLKMNSLQTDDAAMYYCAS   HY
         *  * * * **  *     .  ... * *  ....  ** ..*.*.*.**

CDR3           FR4
              110            120
7F3 Vh   LISTVTAVDY     WGQGTTLTVSS
6c12 Vh  ITTVVGAMDY     WGQGTSVTVSS
12d4 Vh  GYDGLG-FAY     WGQGTLVTVSV
                 .     *****  .***
```

Figure 14

ANTI-C5AR ANTIBODIES AND USES THEREOF

CROSS-REFERENCE TO RELATED APPLICATIONS

This application is a national phase filing under 35 U.S.C. §371 of International Patent Application No. PCT/AU03/00084, filed Jan. 24, 2003, which claims the benefit of U.S. Provisional Patent Application No. 60/350,961, filed Jan. 25, 2002, which applications are incorporated herein by reference in their entirety.

FIELD OF THE INVENTION

The present invention relates to antibodies which bind to C5aR and which are useful in diagnostic and therapeutic methods.

BACKGROUND OF THE INVENTION

Proteolysis of each of the complement proteins C3-C5 gives rise to aminoterminal cationic fragments with signalling molecules called anaphylatoxins (6-9). The most potent of these, C5a, elicits the broadest responses. Considering the components of the inflammatory response as margination and infiltration of leukocytes, release of granule-bound proteolytic enzymes, production of activated oxygen and nitrogen-derived radicals, changes in blood flow and capillary leakage, along with the ability to contract smooth muscle, the C5a molecule is the "complete" pro-inflammatory mediator. At sub-nanomolar to nanomolar levels, the C5a molecule elicits chemotaxis of all myeloid lineages (neutrophils, eosinophils and basophils, macrophages and monocytes), and causes vascular permeability which is markedly potentiated by prostaglandins and circulating leukocytes. Higher nanomolar concentrations elicit degranulation and activation of NADPH oxidase. This breadth of bioactivity contrasts with other inflammatory mediators. C5a has been implicated in the pathogenesis of rheumatoid arthritis, psoriasis, sepsis, reperfusion injury, and adult respiratory distress syndrome [1, 2].

The activities of C5a are mediated by the binding of the C5a to its receptor (C5aR). C5aR belongs to the family of seven transmembrane G-protein-coupled receptors. C5aR is a high affinity receptor for C5a, with a Kd of ~1 nM, and is located on a number of different cell types including leukocytes. The number of receptors per cell is extremely high, up to 200,000 sites per leukocyte. Biological activation of the receptor occurs over the range that saturates binding.

C5aR comprises an extended N-terminal extracellular domain. This large N-terminal domain is typical of G-protein coupled receptors which bind peptides including the IL-8 and fMet-Leu-Phe (FMLP) receptor families. The C5aR structure conforms to the seven transmembrane receptor family, with the extracellular N-terminus being followed by seven transmembrane helices connected by interhelical domains alternating as intracellular and extracellular loops, and ending with an intracellular C-terminal domain.

Inhibition of the C5a responses with C5aR antagonists should reduce the acute inflammatory response mediated via C5a without affecting other complement components. To this end, C5aR peptide antagonists and anti-C5a receptor antibodies have been previously described [3-7]. For example, WO95/00164 describes antibodies directed against an N-terminal peptide (residues 9-29) of the C5a receptor. Currently, however, alternative and/or improved C5aR antagonists are desirable.

SUMMARY OF THE INVENTION

The present inventors have now developed novel monoclonal antibodies which are reactive with regions of C5aR other than the N-terminal domain and which are highly effective in inhibiting C5a binding to C5aR. These monoclonal antibodies have been designated 7F3, 6C12 and 12D4.

Accordingly, in one aspect the present invention provides an antibody that is reactive with an extracellular loop(s) of C5aR other than the N-terminal domain, wherein the antibody reduces or inhibits the binding of C5a to C5aR.

By "extracellular loop" we mean either the first extracellular loop (residues 95 to 110), the second extracellular loop (residues 175 to 206) or the third extracellular loop (residues 265 to 283) of C5aR.

In one preferred embodiment, the antibody is reactive with an epitope comprising the second extracellular loop (residues 175 to 206) of C5aR.

In another aspect, the present invention provides an antibody that is reactive with the same epitope of C5aR as MAb 7F3, wherein the antibody reduces or inhibits the binding of C5a to C5aR.

In another aspect, the present invention provides an antibody that is reactive with the same epitope of C5aR as MAb 6C12, wherein the antibody reduces or inhibits the binding of C5a to C5aR.

In another aspect, the present invention provides an antibody that is reactive with the same epitope of C5aR as MAb 12D4, wherein the antibody reduces or inhibits the binding of C5a to C5aR.

In another aspect, the present invention provides an antibody that binds to C5aR, wherein the antibody competitively inhibits the binding of MAb 7F3 to C5aR.

In another aspect, the present invention provides an antibody that binds to C5aR, wherein the antibody competitively inhibits the binding of MAb 6C12 to C5aR.

In another aspect, the present invention provides an antibody that binds to C5aR, wherein the antibody competitively inhibits the binding of MAb 12D4 to C5aR.

In a preferred embodiment of these aspects of the invention, the comparative binding specificity is determined by antibody-antibody competition assays in the presence of C5aR or a polypeptide comprising an extracellular loop of C5aR.

In yet another aspect, the present invention provides an antibody comprising substantially the same light and/or heavy chain sequences as shown in SEQ ID NO:19 and SEQ ID NO:21 respectively, wherein the antibody reduces or inhibits the binding of C5a to C5aR.

In yet another aspect, the present invention provides an antibody comprising at least one CDR loop sequence which is substantially the same as a variable heavy chain CDR1, CDR2 or CDR3 loop sequence as shown in SEQ ID NO:26, SEQ ID NO:27 or SEQ ID NO:28 respectively, wherein the antibody reduces or inhibits the binding of C5a to C5aR.

In a preferred embodiment, the antibody comprises at least two, more preferably at least three CDR loop sequences which are substantially the same as the variable heavy chain CDR1, CDR2 or CDR3 loop sequences shown in SEQ ID NO:26, SEQ ID NO:27 and SEQ ID NO:28 respectively.

In a further preferred embodiment, the antibody comprises at least one CDR loop sequence substantially as defined by amino acid residues 24 to 39, 55 to 61 or 94 to 102 of the variable light chain sequence shown in SEQ ID NO:19. Preferably, the antibody comprises at least two, more preferably at least three CDR loop sequences substantially as defined by amino acid residues 24 to 39, 55 to 61 and 94 to 102 of the variable light chain sequence shown in SEQ ID NO:19.

In yet another aspect, the present invention provides an antibody comprising substantially the same light and/or heavy chain sequences as shown in SEQ ID NO:15 and SEQ ID NO:17 respectively, wherein the antibody reduces or inhibits the binding of C5a to C5aR.

In yet another aspect, the present invention provides an antibody comprising at least one CDR loop sequence which is substantially the same as a variable heavy chain CDR1, CDR2 or CDR3 loop sequence as shown in SEQ ID NO:29, SEQ ID NO:30 or SEQ ID NO:31 respectively, wherein the antibody reduces or inhibits the binding of C5a to C5aR.

In a preferred embodiment, the antibody comprises at least two, more preferably at least three CDR loop sequences which are substantially the same as the variable heavy chain CDR1, CDR2 or CDR3 loop sequences shown in SEQ ID NO:29, SEQ ID NO:30 and SEQ ID NO:31 respectively.

In a further preferred embodiment, the antibody comprises at least one CDR loop sequence substantially as defined by amino acid residues 24 to 39, 55 to 61 or 94 to 102 of the variable light chain sequence shown in SEQ ID NO:15. Preferably, the antibody comprises at least two, more preferably at least three CDR loop sequences substantially as defined by amino acid residues 24 to 39, 55 to 61 and 94 to 102 of the variable light chain sequence shown in SEQ ID NO:15.

In yet another aspect, the present invention provides an antibody comprising substantially the same light and/or heavy chain sequences as shown in SEQ ID NO:23 and SEQ ID NO:25 respectively, wherein the antibody reduces or inhibits the binding of C5a to C5aR.

In yet another aspect, the present invention provides an antibody comprising at least one CDR loop sequence which is substantially the same as a variable heavy chain CDR1, CDR2 or CDR3 loop sequence as shown in SEQ ID NO:32, SEQ ID NO:33 or SEQ ID NO:34 respectively, wherein the antibody reduces or inhibits the binding of C5a to C5aR.

In a preferred embodiment, the antibody comprises at least two, more preferably at least three CDR loop sequences which are substantially the same as the variable heavy chain CDR1, CDR2 or CDR3 loop sequences shown in SEQ ID NO:32, SEQ ID NO:33 and SEQ ID NO:34 respectively.

In a further preferred embodiment, the antibody comprises at least one CDR loop sequence substantially as defined by amino acid residues 24 to 39, 55 to 61 or 94 to 102 of the variable light chain sequence shown in SEQ ID NO:23. Preferably, the antibody comprises at least two, more preferably at least three CDR loop sequences substantially as defined by amino acid residues 24 to 39, 55 to 61 and 94 to 102 of the variable light chain sequence shown in SEQ ID NO:23.

In a preferred embodiment of the present invention, the C5aR is human C5aR.

In one embodiment of the present invention, the antibody also inhibits neutrophil activation by other neutrophil chemoattractants, particularly CXCR1 and CXCR2 ligands such as IL-8.

In one preferred embodiment of the present invention, the antibody is a monoclonal or recombinant antibody. Preferably, the monoclonal or recombinant antibody is a chimeric antibody or a humanized antibody.

The antibody may be of any isotype. In a further preferred embodiment of the present invention, however, the antibody is a class IgG2a or class IgG3 antibody.

In another preferred embodiment of the invention, the antibody is a monoclonal antibody selected from the group consisting of MAb 7F3, MAb 6C12 and MAb 12D4.

In a further aspect, the present invention provides a hybridoma as deposited with ECACC under accession number 00110609.

In a further aspect, the present invention provides a hybridoma as deposited with ECACC under accession number 02090226.

In a further aspect, the present invention provides a hybridoma as deposited with ECACC under accession number 02090227.

It will be appreciated that various chemical derivatives of the antibodies of the invention may also be produced. For example, immunoconjugates consisting of an antibody of the present invention bound to a label such as a radioisotope or other tracer molecule can be made by techniques known in the art. Alternatively, the antibody may be bound to a therapeutically useful molecule which is targeted to its desired site of action by virtue of the antibody's binding specificity.

Accordingly, in yet another aspect the present invention provides a conjugate comprising an antibody of the present invention and a therapeutic agent.

It will be appreciated that a range of therapeutic agents may be used in the context of the present invention. Preferred therapeutic agents include agents that mediate cell death or protein inactivation. The therapeutic agent may be any of a large number of toxins known in the art. The toxin may be *Pseudomonas* exotoxin or a derivative thereof. In a preferred embodiment, the toxin is PE40.

In yet another aspect the present invention provides a conjugate comprising an antibody of the present invention and a detectable label.

The detectable label may be any suitable label known in the art. For example, the label may be a radiolabel, a fluorescent label, an enzymatic label or contrast media.

In yet another aspect the present invention provides an isolated nucleic acid molecule, the nucleic acid molecule comprising a sequence encoding an antibody of the present invention.

In yet another aspect, the present invention provides a composition comprising a antibody of the present invention and a pharmaceutically acceptable carrier.

In yet another aspect the present invention provides a method for inhibiting the interaction of a cell bearing C5aR with a ligand thereof, the method comprising exposing the cell to an antibody of the present invention.

In yet another aspect the present invention provides a method for inhibiting C5aR activity in a cell, the method comprising exposing the cell to an antibody of the present invention.

In yet another aspect the present invention provides a method of treating a disorder involving neutrophil migration in a subject, the method comprising administering to the subject an antibody of the present invention.

It will be appreciated by those skilled in the art that the antibodies of the present invention may also be used to detect, quantitate and/or localise cells expressing C5aR.

Accordingly, in a further aspect the present invention provides a method for diagnosing a disorder involving neutrophil migration in a subject, the method comprising contacting a sample obtained from the subject with a conjugate of the present invention, and detecting immunospecific binding between the conjugate and the sample.

A variety of immunoassays may be used in the methods of diagnosis. Such immunoassays include competitive and non-competitive assay systems using techniques such as radioimmunoassays, ELISA, "sandwich" immunoassays, precipitin reactions, gel diffusion precipitin reactions, immunodiffusion assays, agglutination assays, complement fixation assays, immunoradiometric assays, fluorescent immunoassays and the like. Both in vitro and in vivo assays can be used.

The sample obtained from the subject may comprise any bodily fluid, such as peripheral blood, plasma, lymphatic fluid, peritoneal fluid, cerebrospinal fluid, or pleural fluid, or any body tissue. In vitro binding may be performed using histological specimens or subfractions of tissue or fluid. In vivo binding may be achieved by administering the conjugate by any means known in the art (such as intravenous, intraperitoneal, intrasarterial, etc.) such that immunospecific binding may be detected.

In addition, imaging techniques may be used, in which an antibody of the first aspect is bound to a suitable imaging label. The labeled antibody may be administered in vivo to determine the localisation of C5aR in a subject.

Accordingly, in a further aspect the present invention provides a method for diagnosing a disorder involving neutrophil migration in a subject, the method comprising administering to the subject an antibody of the present invention labeled with an imaging agent under conditions so as to form a complex between the antibody and cells presenting C5aR in the subject, and imaging the complex.

In one preferred embodiment of the present invention, the a disorder involving neutrophil migration is a C5aR mediated disorder. Preferably, the disorder is an immunopathological disorder.

In a further aspect, the present invention provides a method for delivering a therapeutic agent to a site of inflammation in a subject, the method comprising administering to the subject a conjugate of the present invention.

In a further aspect the present invention provides a method for introducing genetic material into cells presenting C5aR, the method comprising contacting the cells with an antibody of the present invention, wherein the antibody is attached to or associated with genetic material.

In a preferred embodiment, cells presenting C5aR are selected from the group consisting of granulocytes, leukocytes, such as monocytes, macrophages, basophils and eosinophils, mast cells and lymphocytes including T cells, dendritic cells, and non-myeloid cells such as endothelial cells and smooth muscle cells.

Also encompassed by the present invention are methods of identifying additional ligands or other substances which bind C5aR, including inhibitors and/or promoters of mammalian C5aR function. For example, agents having the same or a similar binding specificity as that of an antibody of the present invention or functional fragment thereof can be identified by a competition assay with said antibody or fragment. Thus, the present invention also encompasses methods of identifying ligands or other substances which bind C5aR, including inhibitors (e.g., antagonists) or promoters (e.g., agonists) of receptor function. In one embodiment, cells which naturally express C5aR or suitable host cells which have been engineered to express C5aR or variant encoded by a nucleic acid introduced into said cells are used in an assay to identify and assess the efficacy of ligands, inhibitors or promoters of receptor function. Such cells are also useful in assessing the function of the expressed receptor protein or polypeptide.

BRIEF DESCRIPTION OF THE FIGURES

FIG. 11 shows an alignment of the variable light chain DNA sequences for MAbs 7F3, 6C12 and 12D4.

FIG. 12 shows an alignment of the variable heavy chain DNA sequences for MAbs 7F3, 6C12 and 12D4.

FIG. 13 shows an alignment of the variable light chain protein sequences for MAbs 7F3, 6C12 and 12D4.

FIG. 14 shows an alignment of the variable heavy chain protein sequences for MAbs 7F3, 6C12 and 12D4.

KEY TO SEQUENCE LISTINGS

Figure 1:
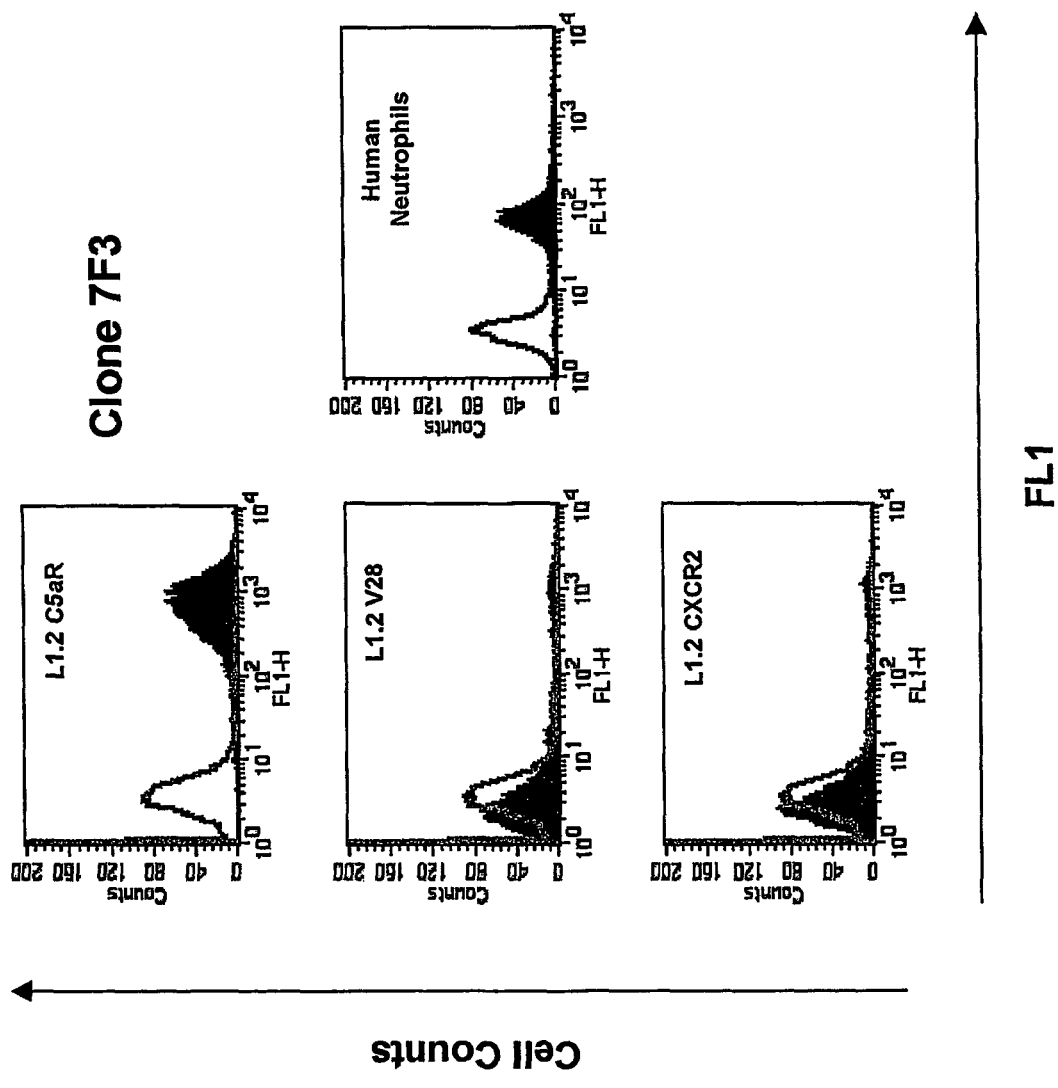
FIG. 1 shows the results of flow cytometry analysis of monoclonal antibody 7F3. These results show that 7F3 reacts specifically with L1.2 cells transfected with C5aR.

| | |
|---|---|
| SEQ ID NO: 1 | Human C5aR protein sequence |
| SEQ ID NO: 2 | PCR primer for 6C12 variable light chain |
| SEQ ID NO: 3 | PCR primer for 6C12 variable light chain |
| SEQ ID NO: 4 | PCR primer for 6C12 variable heavy chain |
| SEQ ID NO: 5 | PCR primer for 6C12 variable heavy chain |
| SEQ ID NO: 6 | PCR primer for 7F3 variable light chain |
| SEQ ID NO: 7 | PCR primer for 7F3 variable light chain |
| SEQ ID NO: 8 | PCR primer for 7F3 variable heavy chain |
| SEQ ID NO: 9 | PCR primer for 7F3 variable heavy chain |
| SEQ ID NO: 10 | PCR primer for 12D4 variable light chain |
| SEQ ID NO: 11 | PCR primer for 12D4 variable light chain |
| SEQ ID NO: 12 | FOR primer for 12D4 variable heavy chain |
| SEQ ID NO: 13 | FOR primer for 12D4 variable heavy chain |
| SEQ ID NO: 14 | 6C12 variable light chain (DNA) sequence |
| SEQ ID NO: 15 | 6C12 variable light chain (protein) sequence |
| SEQ ID NO: 16 | 6C12 variable heavy chain (DNA) sequence |
| SEQ ID NO: 17 | 6C12 variable heavy chain (protein) sequence |
| SEQ ID NO: 18 | 7F3 variable light chain (DNA) sequence |
| SEQ ID NO: 19 | 7F3 variable light chain (protein) sequence |
| SEQ ID NO: 20 | 7F3 variable heavy chain (DNA) sequence |
| SEQ ID NO: 21 | 7F3 variable heavy chain (protein) sequence |
| SEQ ID NO: 22 | 12D4 variable light chain (DNA) sequence |
| SEQ ID NO: 23 | 12D4 variable light chain (protein) sequence |
| SEQ ID NO: 24 | 12D4 variable heavy chain (DNA) sequence |
| SEQ ID NO: 25 | 12D4 variable heavy chain (protein) sequence |
| SEQ ID NO: 26 | 7F3 variable heavy chain CDR1 loop |
| SEQ ID NO: 27 | 7F3 variable heavy chain CDR2 loop |
| SEQ ID NO: 28 | 7F3 variable heavy chain CDR3 loop |
| SEQ ID NO: 29 | 6C12 variable heavy chain CDR1 loop |
| SEQ ID NO: 30 | 6C12 variable heavy chain CDR2 loop |
| SEQ ID NO: 31 | 6C12 variable heavy chain CDR3 loop |
| SEQ ID NO: 32 | 12D4 variable heavy chain CDR1 loop |
| SEQ ID NO: 33 | 12D4 variable heavy chain CDR2 loop |
| SEQ ID NO: 34 | 12D4 variable heavy chain CDR3 loop |

DETAILED DESCRIPTION OF THE INVENTION

C5aR Structure

The amino acid sequence of human C5aR is provided in SEQ ID NO:1.

The various domains of human C5aR are defined as follows:

| amino acids | 1-37 | extracellular domain - N-terminus |
|---|---|---|
| amino acids | 38-61 | transmembrane domain |
| amino acids | 62-71 | intracellular domain |
| amino acids | 72-94 | transmembrane domain |
| amino acids | 95-110 | extracellular domain - extracellular loop 1 |
| amino acids | 111-132 | transmembrane domain |
| amino acids | 133.-.149 | intracellular domain |
| amino acids | 150.-.174 | transmembrane domain |
| amino acids | 175.-.206 | extracellular domain - extracellular loop 2 |
| amino acids | 207.-.227 | transmembrane domain |
| amino acids | 228.-.242 | intracellular domain |
| amino acids | 243.-.264 | transmembrane domain |
| amino acids | 265.-.283 | extracellular domain - extracellular loop 3 |
| amino acids | 284.-.307 | transmembrane domain |
| amino acids | 308.-.350 | intracellular domain - C-terminus |

Micro-Organism Deposit Details

The hybridoma which produces the monoclonal antibody designated 7F3 was deposited on 6 Nov. 2000 with ECACC under accession number 00110609 (European Collection of Cell Cultures (ECACC), Porton Down, Salisbury, Wiltshire, SP4 0JG, United Kingdom).

The hybridoma which produces the monoclonal antibody designated 6C12 (6C12 M12) was deposited on 2 Sep. 2002 with ECACC under accession number 02090226 (European Collection of Cell Cultures (ECACC), Porton Down, Salisbury, Wiltshire, SP4 0JG, United Kingdom).

The hybridoma which produces the monoclonal antibody designated 12D4 (12D4-N17) was deposited on 8 Sep. 2004 with ECACC under accession number 04090801.

These deposits were made under the provisions of the Budapest Treaty on the International Recognition of the Deposit of Microorganisms for the Purpose of Patent Procedure and the Regulations thereunder. This assures maintenance of viable cultures for 30 years from the date of deposit and for at least five (5) years after the most recent request for the furnishing of a sample of the deposit received by the depository or for the enforceable life of the patent, whichever is longer. The organisms will be made available by ECACC under the terms of the Budapest Treaty which assures permanent and unrestricted availability of the progeny of the culture to the public upon issuance of the pertinent patent.

The assignee of the present application has agreed that if the culture deposit should die or be lost or destroyed when cultivated under suitable conditions, it will be promptly replaced on notification with a viable specimen of the same culture. Availability of a deposited strain is not to be construed as a license to practice the invention in contravention of the rights granted under the authority of any government in accordance with its patent laws.

Monoclonal and Recombinant Antibodies

Murine monoclonal antibodies specific for C5aR, designated 7F3, 6C12 and 12D4, have been produced by the present inventors as described herein. Surprisingly, these monoclonal antibodies (MAbs) are able to substantially or completely block C5a binding to C5aR. In particular, MAb 7F3 is fully neutralising.

In contrast to other known anti-C5aR antibodies, MAbs 7F3, 6C12 and 12D4 are reactive with regions of C5aR other than the N-terminal region. It is believed that MAbs 7F3, 6C12 and 12D4 are primarily reactive with the second extracellular loop (residues 175 to 206) of C5aR. For example, MAb 12D4 reactivity with C5aR is almost completely abolished by mutation of the 2nd extracellular loop residues 181 and 192 from tyrosine to phenylalanine. This inhibition was observed in binding studies involving the C5aR mutant L2-FF (Farzan et al., J. Exp. Med., 193:1059-1065, 2001).

Due to the likely conformation and close proximity of the extracellular loops and N-terminal domain, the MAbs may also simultaneously bind to a region of one of the other extracellular loops or the N-terminal domain.

Surprisingly, it has been shown that MAbs 7F3, 6C12 and 12D4 are also capable of inhibiting activation of neutrophils by other chemoattractant ligands. Examples of these other chemoattractant ligands include the CXCR1 and CXCR2 ligands IL-8, ENA-78 and GPC-2. This ability to inhibit the function of different chemoattractant receptors provides an unusual and unexpected advantage over other known anti-C5aR molecules. In particular, anti-C5aR molecules that are able to inhibit the function of multiple neutrophil chemoattractant receptors are likely to be highly efficient therapeutic agents in the treatment of immunopathological disorders.

In one aspect, the present invention provides antibodies that bind to an extracellular loop, preferably the second extracellular loop of C5aR, either alone or in conjunction with other loops or domains. In a preferred aspect, the invention provides antibodies that bind to C5aR and have epitopic specificity the same or similar to that of any one of MAbs 7F3, 6C12 or 12D4.

The term "antibody" as used in this invention includes intact molecules as well as fragments thereof, such as Fab, F(ab')2, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')2, the fragment of the antibody that can be obtained by treating whole antibody with the enzyme pepsin without subsequent reduction; F(ab)2 is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies of the present invention can be prepared using cells expressing C5sR, intact C5aR or fragments containing one or more extracellular loops as the immunizing antigen. A peptide used to immunize an animal can be derived from translated cDNA or chemical synthesis and is purified and conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide may then be used to immunize the animal (e.g., a mouse or a rabbit).

If desired, polyclonal antibodies can be further purified, for example, by binding to and elution from a matrix to which the peptide to which the antibodies were raised is bound.

Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1991, incorporated by reference).

Monoclonal antibodies may be prepared using any technique which provides for the production of antibody molecules by continuous cell lines in culture, such as, for example, the hybridoma technique, the human B-cell hybridoma technique, and the EBV-hybridoma technique (Kohler et al. Nature 256, 495-497, 1975; Kozbor et al., J. Immunol. Methods 81, 31-42, 1985; Cote et al., Proc. Natl. Acad. Sci. USA 80, 2026-2030, 1983; Cole et al., Mol. Cell Biol. 62, 109-120, 1984).

Methods known in the art allow antibodies exhibiting binding for a C5aR extracellular loop to be identified and isolated from antibody expression libraries. For example, a method for the identification and isolation of an antibody binding domain which exhibits binding to a C5aR extracellular loop is the bacterio-phage a vector system. This vector system has been used to express a combinatorial library of Fab fragments from the mouse antibody repertoire in *Escherichia coli* (Huse, et al., Science, 246:1275-1281, 1989) and from the human antibody repertoire (Mullinax, et al., Proc. Nat. Acad. Sci., 87:8095-8099, 1990). This methodology can also be applied to hybridoma cell lines expressing monoclonal antibodies with binding for a preselected ligand. Hybridomas which secrete a desired monoclonal antibody can be produced in various ways using techniques well understood by those having ordinary skill in the art and will not be repeated here. Details of these techniques are described in such references as Monoclonal Antibodies-Hybridomas: A New Dimension in Biological Analysis, Edited by Roger H. Kennett, et al., Plenum Press, 1980; and U.S. Pat. No. 4,172,124, incorporated by reference.

In addition, methods of producing chimeric antibody molecules with various combinations of "humanized" antibodies are known in the art and include combining murine variable regions with human constant regions (Cabily, et al. Proc. Natl. Acad. Sci. USA, 81:3273, 1984), or by grafting the murine-antibody complementarity determining regions (CDRs) onto the human framework (Riechmann, et al., Nature 332:323, 1988).

This invention further provides chimeric antibodies of the anti-C5aR antibodies of the present invention or biologically active fragments thereof. As used herein, the term "chimeric antibody" refers to an antibody in which the variable regions of antibodies derived from one species are combined with the constant regions of antibodies derived from a different species or alternatively refers to CDR grafted antibodies. Chimeric antibodies are constructed by recombinant DNA technology, and are described in Shaw, et al., J. Immun., 138:4534 (1987), Sun, L K., et al., Proc. Natl. Acad. Sci. USA, 84:214-218 (1987), for example.

Any of the above described antibodies or biologically active antibody fragments can be used to generate CDR grafted and chimeric antibodies. "CDR" or "complementarity determining region" or "hypervariable region" is defined as the amino acid sequences on the light and heavy chains of an antibody which form the three-dimensional loop structure that contributes to the formation of the antigen binding site.

As used herein, the term "CDR grafted" antibody refers to an antibody having an amino acid sequence in which at least parts of one or more CDR sequences in the light and/or variable domain have been replaced by analogous parts of CDR sequences from an antibody having a different binding specificity for a given antigen or receptor.

The terms "light chain variable region" and "heavy chain variable region" refer to the regions or domains at the N-terminal portion of the light and heavy chains respectively which have a varied primary amino acid sequence for each antibody. The variable region of the antibody consists of the amino terminal domain of the light and heavy chains as they fold together to form a three-dimensional binding site for an antibody.

The analogous CDR sequences are said to be "grafted" onto the substrate or recipient antibody. The "donor" antibody is the antibody providing the CDR sequence, and the antibody receiving the substituted sequences is the "substrate" antibody. One of skill in the art can readily produce these CDR grafted antibodies using the teachings provided herein in combination with methods well known in the art (see Borrebaeck, C. A., Antibody Engineering: A Practical Guide, W.H. Freeman and Company, New York, 1992, incorporated by reference).

The invention also provides cell lines which produce monoclonal antibodies of the invention. The isolation of cell lines producing monoclonal antibodies of the invention can be accomplished using routine screening techniques which permit determination of the elementary reaction pattern of the monoclonal antibody of interest. Thus, if a monoclonal antibody being tested binds C5aR and blocks C5a-mediated biological activity, then the monoclonal antibody being tested and the monoclonal antibody produced by the cell lines of the invention are equivalent.

Antibodies with an epitopic specificity which is the same as or similar to that of MAbs 7F3, 6C12 or 12D4 can be identified by their ability to compete with that particular MAb for binding to C5aR (e.g. to cells bearing C5aR, such as transfectants bearing C5aR, monocytes, dendritic cells, macrophages and basophils). Using receptor chimeras (Rucker et al., Cell 87:437-446 (1996)) or other techniques known to those skilled in the art, the binding site of any one of MAbs 7F3, 6C12 or 12D4 may be mapped.

It is also possible to determine, without undue experimentation, if a monoclonal antibody has the same specificity as a monoclonal antibody of the invention by ascertaining whether the former prevents the latter from binding to a peptide comprising a C5aR extracellular loop. If the monoclonal antibody being tested competes with the monoclonal antibody of the invention, as shown by a decrease in binding by the monoclonal antibody of the invention, then the two monoclonal antibodies bind to the same, or a closely related, epitope.

Still another way to determine whether a monoclonal antibody has the specificity of a monoclonal antibody of the invention is to pre-incubate the monoclonal antibody being tested with a peptide to which the antibody is presumed to be reactive, and then add the monoclonal antibody of the invention to determine if the monoclonal antibody of the invention is inhibited in its ability to bind the peptide. If the monoclonal antibody of the invention is inhibited then, in all likelihood, the monoclonal antibody being tested has the same, or functionally equivalent, epitopic specificity as the monoclonal antibody of the invention. Screening of monoclonal antibodies of the invention, can also be carried out utilizing suitable peptides and determining whether the monoclonal antibody blocks C5a from binding to C5aR.

By using the monoclonal antibodies of the invention, it is possible to produce anti-idiotypic antibodies which can be used to screen monoclonal antibodies to identify whether the antibody has the same binding specificity as a monoclonal antibody of the invention. These antibodies can also be used for immunization purposes (Herlyn, et al., Science, 232:100, 1986). Such anti-idiotypic antibodies can be produced using well-known hybridoma techniques (Kohler and Milstein, Nature, 256:495, 1975). An anti-idiotypic antibody is an antibody which recognizes unique determinants present on the monoclonal antibody produced by the cell line of interest. These determinants are located in the hypervariable region of the antibody. It is this region (paratope) which binds to a given epitope and, thus, is responsible for the specificity of the antibody. An anti-idiotypic antibody can be prepared by immunizing an animal with the monoclonal antibody of interest. The immunized animal will recognize and respond to the idiotypic determinants of the immunizing antibody and produce an antibody to these idiotypic determinants. By using the anti-idiotypic antibodies of the immunized animal, which are specific for a monoclonal antibody of the invention produced by a cell line which was used to immunize the second animal, it is possible to identify other clones with the same idiotype as the antibody of the hybridoma used for immunization. Idiotypic identity between monoclonal antibodies of two cell lines demonstrates that the two monoclonal antibodies are the same with respect to their recogniition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, the anti-idiotypic monoclonal antibody can be used for immunization, since the anti-idiotype monoclonal antibody binding domain effectively acts as an antigen.

Antibody fragments which contain epitopic binding sites of any one of the MAbs of the present invention can be generated by known techniques. For example, suitable antibody fragments may be obtained by first obtaining mAb 7F3 from the deposited hybridoma and then treating the antibody (eg. by proteolytic digestion) so as to obtain from it the hypervariable region.

Alternatively, the DNA encoding the hypervariable region may be cloned, using standard recombinant DNA procedures such as those described herein, in a suitable host.

Preferred antibodies of the present invention comprise variable regions or one or more CDR loops that are substantially the same as those of MAbs 7F3, 6C12 or 12D4. It will be understood that the variable regions or CDR loops shown in the sequence listings may be modified for use in the present invention. Typically, modifications are made that maintain the binding specificity of the sequence. Conservative substitutions may be made, for example, without affecting the binding specificity of the antibody. Thus, in one embodiment, amino acid substitutions may be made, for example from 1, 2 or 3 to 10, 20 or 30 substitutions provided that the modified sequence retains substantially the same binding specificity. However, in an alternative embodiment, modifications to the amino acid sequences of an antibody of the invention may be made intentionally to reduce the biological activity of the antibody. For example modified antibodies that remain capable of binding to C5aR but lack functional effector domains may be useful as inhibitors of the biological activity of C5aR.

Amino acid substitutions may also include the use of non-naturally occurring analogues, for example to increase blood plasma half-life of a therapeutically administered antibody.

In general, preferably less than 20%, 10% or 5% of the amino acid residues of a variant or derivative are altered as compared with the corresponding variable regions or CDR loops depicted in the sequence listings.

In the context of the present invention, a sequence "substantially the same" as one of the variable regions shown is the sequence listing may include an amino acid sequence which is at least 80%, 85% or 90% identical, preferably at least 95 or 98% identical at the amino acid level over at least 20, preferably at least 50 amino acids with that variable region. Homology should typically be considered with respect to those regions of the sequence known to be essential for binding specificity rather than non-essential neighbouring sequences.

Homology comparisons can be conducted by eye, or more usually, with the aid of readily available sequence comparison programs. These commercially available computer programs can calculate % homology between two or more sequences.

Percentage homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol.

Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSLUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

Humanization of Antibodies

It is preferred that an antibody of the present invention is humanized, that is, an antibody produced by molecular modelling techniques wherein the human content of the antibody is maximised while causing little or no loss of binding affinity attributable to the variable region of the murine antibody. Thus, in one embodiment the invention provides a chimeric antibody comprising the amino acid sequence of a human framework region and of a constant region from a human antibody so as to humanise or render nonimmunogenic the hypervariable region from a mouse monoclonal antibody such as 7F3, C612 or 12D4.

The methods described below are applicable to the humanization of a wide variety of animal antibodies. A two-step approach may be used which involves (a) selecting human antibody sequences that are used as human frameworks for humanization, and (b) determining which variable region residues of the animal monoclonal antibody should be selected for insertion into the human framework chosen.

The first step involves selection of the best available human framework sequences for which sequence information is available. This selection process is based upon the following selection criteria.

(1) Percent Identities

The sequences of the heavy and light chain variable regions of an animal monoclonal antibody that is to be humanized are optimally aligned and compared preferably with all known human antibody heavy and light chain variable region sequences.

Once the sequences are thus compared, residue identities are noted and percent identities are determined. All other factors being equal, it is desirable to select a human antibody which has the highest percent identity with the animal antibody.

(2) Sequence Ambiguitites

The known human antibody chain sequences are then evaluated for the presence of unidentified residues and/or ambiguities, which are sequence uncertainties. The most common of such uncertainties are mistaken identification of an acidic amino acid for an amide amino acid due to loss of ammonia during the sequencing procedure, eg., incorrect identification of a glutamic acid residue, when the residue actually present in the protein was a glutamine residue. All other factors being equal, it is desirable to select a human antibody chain having as few such ambiguities as possible.

(3) Pin-Region Spacing

Antibody chain variable regions contain intra-domain disulfide bridges. The distance (number of residues) between the cysteine residues comprising these bridges is referred to as the Pin-region spacing [Chothia et al, J. Mol. Biol. 196:901 (1987)]. All other factors being equal, it is most desirable that the Pin-region spacing of a human antibody selected be similar or identical to that of the animal antibody. It is also desirable that the human sequence Pin-region spacing be similar to that of a known antibody 3-dimensional structure, to facilitate computer modeling.

Based upon the foregoing criteria, the human antibody (or antibodies) having the best overall combination of desirable characteristics is selected as the framework for humanization of the animal antibody. The heavy and light chains selected may be from the same or different human antibodies.

The second step in the methods of this invention involves determination of which of the animal antibody variable region sequences should be selected for grafting into the human framework. This selection process is based upon the following selection criteria:

(1) Residue Selection

Two types of potential variable region residues are evaluated in the animal antibody sequences, the first of which are called "minimal residues." These minimal residues comprise CDR structural loops plus any additional residues required, as shown by computer modeling, to support and/or orient the CDR structural loops.

The other type of potential variable region residues are referred to as "maximal residues." They comprise the minimal residues plus any additional residues which, as determined by computer modeling, fall within about 10 Å of CDR structural loop residues and possess a water solvent accessible surface [Lee et al, J. Biol. Chem. 55:379 (1971)].

(2) Computer Modeling

To identify potential variable region residues, computer modeling is carried out on (a) the variable region sequences of the animal antibody that is to be humanized, (b) the selected human antibody framework sequences, and (c) all possible recombinant antibodies comprising the human antibody framework sequences into which the various minimal and maximal animal antibody residues have been grafted.

The computer modeling is performed using software suitable for protein modeling and structural information obtained from an antibody that (a) has variable region amino acid sequences most nearly identical to those of the animal antibody and (b) has a known 3-dimensional structure. An example of software that can be used is the SYBYL Biopolymer Module software (Tripos Associates). The antibody from which the structural information can be obtained may be but need not necessarily be a human antibody.

Based upon results obtained in the foregoing analysis, recombinant chains containing the animal variable regions producing a computer modeling structure most nearly approximating that of the animal antibody are selected for humanisation.

Antibody Isotypes

Under certain circumstances, monoclonal antibodies of one isotype might be more preferable than those of another in terms of their diagnostic or therapeutic efficacy. For example, from studies on antibody-mediated cytolysis it is known that unmodified mouse monoclonal antibodies of isotype gamma-2a and gamma-3 are generally more effective in lysing target cells than are antibodies of the gamma-1 isotype. This differential efficacy is thought to be due to the ability of the gamma-2a and gamma-3 isotypes to more actively participate in the cytolytic destruction of the target cells. Particular isotypes of a monoclonal antibody can be prepared secondarily, from a parental hybridoma secreting monoclonal antibody of different isotype, by using the sib selection technique to isolate class-switch variants (Steplewski, et al., Proc. Natl. Acad. Sci. U.S.A., 82:8653, 1985; Spira, et al., J. Immunol. Methods, 74:307, 1984). Thus, the monoclonal antibodies of the invention would include class-switch variants having the specificity of any one of MAbs 7F3, 6C12 and 12D4.

In Vitro Assays

The monoclonal antibodies of the invention are suited for use in vitro, for example, in immunoassays in which they can be utilized in liquid phase or bound to a solid phase carrier. The antibodies may be useful for monitoring the level of C5aR in a sample. Similarly, anti-idiotype antibodies are useful for measuring the level of C5a in a sample. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of C5aR. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

In one embodiment, cells which naturally express C5aR or cells comprising a recombinant nucleic acid sequence which encodes a C5aR or variant thereof are used in binding assays of the present invention. The cells are maintained under conditions appropriate for expression of receptor. The cells are contacted with an antibody or fragment under conditions suitable for binding (e.g., in a suitable binding buffer), and binding is detected by standard techniques. To determine binding, the extent of binding can be determined relative to a suitable control (e.g., compared with background determined in the absence of antibody, compared with binding of a second antibody (i.e., a standard), compared with binding of antibody to untransfected cells). A cellular fraction, such as a membrane fraction, containing receptor or liposomes comprising receptor can be used in lieu of whole cells.

Binding inhibition assays can also be used to identify antibodies or fragments thereof which bind C5aR and inhibit binding of C5a to C5aR or a functional variant. For example, a binding assay can be conducted in which a reduction in the binding of C5a (in the presence of the antibody), as compared to binding of C5a in the absence of the antibody, is detected or measured. A composition comprising an isolated and/or recombinant mammalian C5aR or functional variant thereof can be contacted with C5a and antibody simultaneously, or one after the other, in either order. A reduction in the extent of binding of the ligand in the presence of the antibody, is indicative of inhibition of binding by the antibody. For example, binding of the ligand could be decreased or abolished.

Other methods of identifying the presence of an antibody which binds C5aR are available, such as other suitable binding assays, or methods which monitor events which are triggered by receptor binding, including signaling function and/or stimulation of a cellular response (e.g., leukocyte trafficking). Antibodies which are identified in this manner can be further assessed to determine whether, subsequent to binding, they act to inhibit other functions of C5aR and/or to assess their therapeutic utility.

Signaling Assays

The binding of a ligand or promoter, such as an agonist, to C5aR can result in signaling by this G protein-coupled receptor, and the activity of G proteins as well as other intracellular signaling molecules is stimulated. The induction of signaling function by a compound (e.g., an antibody or fragment thereof) can be monitored using any suitable method. Such an assay can be used to identify antibody agonists of C5aR. The inhibitory activity of an antibody or functional fragment thereof can be determined using a ligand or promoter in the assay, and assessing the ability of the antibody to inhibit the activity induced by ligand or promoter.

G protein activity, such as hydrolysis of GTP to GDP, or later signaling events triggered by receptor binding, such as induction of rapid and transient increase in the concentration of intracellular (cytosolic) free calcium can be assayed by methods known in the art or other suitable methods (see, for example, Neote, K. et al., Cell, 72: 415-425,1993; Van Riper et al., J. Exp. Med., 177: 851-856, 1993; Dahinden, C. A et al., J. Exp. Med., 179: 751-756, 1994).

For example, the functional assay of Sledziewski et al. using hybrid G protein coupled receptors can be used to monitor the ability of a ligand or promoter to bind receptor and activate a G protein (Sledziewski et al., U.S. Pat. No. 5,284,746).

Such assays can be performed in the presence of the antibody or fragment thereof to be assessed, and the ability of the antibody or fragment to inhibit the activity induced by the ligand or promoter is determined using known methods and/or methods described herein.

Chemotaxis and Assays of Cellular Stimulation

Chemotaxis assays can also be used to assess the ability of an antibody or functional fragment thereof to block binding of a ligand to C5aR and/or inhibit function associated with binding of the ligand to the receptor. These assays are based on the functional migration of cells in vitro or in vivo induced by a compound. Chemotaxis can be assessed by any suitable means, for example, in an assay utilizing a 96-well chemotaxis plate, or using other art-recognized methods for assessing chemotaxis. For example, the use of an in vitro transendothelial chemotaxis assay is described by Springer et al.

(Springer et al., WO 94/20142, published Sep. 15, 1994; see also Berman et al., Immunol. Invest. 17: 625-677 (1988)). Migration across endothelium into collagen gels has also been described (Kavanaugh et al., J. Immunol., 146: 4149-4156 (1991)). Stable transfectants of mouse L1-2 pre-B cells or of other suitable host cells capable of chemotaxis may be used in chemotaxis assays.

Generally, chemotaxis assays monitor the directional movement or migration of a suitable cell (such as a leukocyte (e.g., lymphocyte, eosinophil, basophil)) into or through a barrier (e.g., endothelium, a filter), toward increased levels of a compound, from a first surface of the barrier toward an opposite second surface. Membranes or filters provide convenient barriers, such that the directional movement or migration of a suitable cell into or through a filter, toward increased levels of a compound, from a first surface of the filter toward an opposite second surface of the filter, is monitored. In some assays, the membrane is coated with a substance to facilitate adhesion, such as ICAM-1, fibronectin or collagen. Such assays provide an in vitro approximation of leukocyte "homing".

For example, one can detect or measure inhibition of the migration of cells in a suitable container (a containing means), from a first chamber into or through a microporous membrane into a second chamber which contains an antibody to be tested, and which is divided from the first chamber by the membrane. A suitable membrane, having a suitable pore size for monitoring specific migration in response to compound, including, for example, nitrocellulose, polycarbonate, is selected. For example, pore sizes of about 3-8 microns, and preferably about 5-8 microns can be used. Pore size can be uniform on a filter or within a range of suitable pore sizes.

To assess migration and inhibition of migration, the distance of migration into the filter, the number of cells crossing the filter that remain adherent to the second surface of the filter, and/or the number of cells that accumulate in the second chamber can be determined using standard techniques (e.g., microscopy). In one embodiment, the cells are labeled with a detectable label (e.g., radioisotope, fluorescent label, antigen or epitope label), and migration can be assessed in the presence and absence of the antibody or fragment by determining the presence of the label adherent to the membrane and/or present in the second chamber using an appropriate method (e.g., by detecting radioactivity, fluorescence, immunoassay). The extent of migration induced by an antibody agonist can be determined relative to a suitable control (e.g., compared to background migration determined in the absence of the antibody, compared to the extent of migration induced by a second compound (i.e., a standard), compared with migration of untransfected cells induced by the antibody). In one embodiment, particularly for T cells, monocytes or cells expressing C5aR, transendothelial migration can be monitored. In this embodiment, transmigration through an endothelial cell layer is assessed. To prepare the cell layer, endothelial cells can be cultured on a microporous filter or membrane, optionally coated with a substance such as collagen, fibronectin, or other extracellular matrix proteins, to facilitate the attachment of endothelial cells. Preferably, endothelial cells are cultured until a confluent monolayer is formed. A variety of mammalian endothelial cells can are available for monolayer formation, including for example, vein, artery or microvascular endothelium, such as human umbilical vein endothelial cells (Clonetics Corp, San Diego, Calif.). To assay chemotaxis in response to a particular mammalian receptor, endothelial cells of the same mammal are preferred; however endothelial cells from a heterologous mammalian species or genus can also be used.

Generally, the assay is performed by detecting the directional migration of cells into or through a membrane or filter, in a direction toward increased levels of a compound, from a first surface of the filter toward an opposite second surface of the filter, wherein the filter contains an endothelial cell layer on a first surface. Directional migration occurs from the area adjacent to the first surface, into or through the membrane, towards a compound situated on the opposite side of the filter. The concentration of compound present in the area adjacent to the second surface, is greater than that in the area adjacent to the first surface.

In one embodiment used to test for an antibody inhibitor, a composition comprising cells capable of migration and expressing C5aR can be placed in the first chamber. A composition comprising one or more ligands or promoters capable of inducing chemotaxis of the cells in the first chamber (having chemoattractant function) is placed in the second chamber. Preferably shortly before the cells are placed in the first chamber, or simultaneously with the cells, a composition comprising the antibody to be tested is placed, preferably, in the first chamber. Antibodies or functional fragments thereof which can bind receptor and inhibit the induction of chemotaxis, by a ligand or promoter, of the cells expressing C5aR in this assay are inhibitors of receptor function (e.g., inhibitors of stimulatory function). A reduction in the extent of migration induced by the ligand or promoter in the presence of the antibody or fragment is indicative of inhibitory activity. Separate binding studies could be performed to determine whether inhibition is a result of binding of the antibody to receptor or occurs via a different mechanism.

In vivo assays which monitor leukocyte infiltration of a tissue, in response to injection of a compound (e.g., chemokine or antibody) in the tissue, are described below (see Models of Inflammation). These models of in vivo homing measure the ability of cells to respond to a ligand or promoter by emigration and chemotaxis to a site of inflammation and to assess the ability of an antibody or fragment thereof to block this emigration.

In addition to the methods described, the effects of an antibody or fragment on the stimulatory function of C5aR can be assessed by monitoring cellular responses induced by active receptor, using suitable host cells containing receptor.

Identification of Additional Ligands, Inhibitors and/or Promoters of C5aR

The assays described above, which can be used to assess binding and function of the antibodies and fragments of the present invention, can be adapted to identify additional ligands or other substances which bind C5aR or functional variant thereof, as well as inhibitors and/or promoters of C5aR function. For example, agents having the same or a similar binding specificity as that of an antibody of the present invention or functional portion thereof can be identified by a competition assay with said antibody or portion thereof. Thus, the present invention also encompasses methods of identifying ligands of the receptor or other substances which bind C5aR, as well as inhibitors (e.g., antagonists) or promoters (e.g., agonists) of receptor function. In one embodiment, cells bearing a C5aR protein or functional variant thereof (e.g., leukocytes, cell lines or suitable host cells which have been engineered to express a mammalian C5aR protein or functional variant encoded by a nucleic acid introduced into said cells) are used in an assay to identify and assess the efficacy of ligands or other substances which bind receptor, including inhibitors or promoters of receptor function. Such cells are also useful in assessing the function of the expressed receptor protein or polypeptide.

According to the present invention, ligands and other substances which bind receptor, inhibitors and promoters of receptor function can be identified in a suitable assay, and further assessed for therapeutic effect. Antagonists of receptor function can be used to inhibit (reduce or prevent) receptor activity, and ligands and/or agonists can be used to induce (trigger or enhance) normal receptor function where indicated. Thus, the present invention provides a method of treating inflammatory diseases, including autoimmune disease and graft rejection, comprising administering an antagonist of receptor function to an individual (e.g., a mammal). The present invention further provides a method of stimulating receptor function by administering a novel ligand or agonist of receptor function to an individual, providing a new approach to selective stimulation of leukocyte function, which is useful, for example, in the treatment of infectious diseases and cancer.

As used herein, a "ligand" of a C5aR protein refers to a particular class of substances which bind to a mammalian C5aR protein, including natural ligands and synthetic and/or recombinant forms of natural ligands. In a preferred embodiment, ligand binding of a C5aR protein occurs with high affinity.

As used herein, an "antagonist" is a substance which inhibits (decreases or prevents) at least one function characteristic of a C5aR protein such as a binding activity (e.g., ligand binding, promoter binding, antibody binding), a signaling activity (e.g., activation of a mammalian G protein, induction of rapid and transient increase in the concentration of cytosolic free calcium) and/or cellular response function (e.g., stimulation of chemotaxis, exocytosis or inflammatory mediator release by leukocytes). The term antagonist encompasses substances which bind receptor (e.g., an antibody, a mutant of a natural ligand, small molecular weight organic molecules, other competitive inhibitors of ligand binding), and substances which inhibit receptor function without binding thereto (e.g., an anti-idiotypic antibody).

As used herein, an "agonist" is a substance which promotes (induces, causes, enhances or increases) at least one function characteristic of a C5aR protein such as a binding activity (e.g., ligand, inhibitor and/or promoter binding), a signaling activity (e.g., activation of a mammalian G protein, induction of rapid and transient increase in the concentration of cytosolic free calcium) and/or a cellular response function (e.g., stimulation of chemotaxis, exocytosis or inflammatory mediator release by leukocytes). The term agonist encompasses substances which bind receptor (e.g., an antibody, a homolog of a natural ligand from another species), and substances which promote receptor function without binding thereto (e.g., by activating an associated protein). In a preferred embodiment, the agonist is other than a homolog of a natural ligand.

Thus, the invention also relates to a method of detecting or identifying an agent which binds C5aR or ligand binding variant thereof, including ligands, antagonists, agonists, and other substances which bind C5aR or functional variant. According to the method, an agent to be tested, an antibody or antigen-binding fragment of the present invention (e.g. an antibody having an epitopic specificity which is the same as or similar to that of 7F3, and antigen-binding fragments thereof) and a composition comprising a C5aR or a ligand binding variant thereof can be combined. The foregoing components are combined under conditions suitable for binding of the antibody or antigen-binding fragment to C5aR, and binding of the antibody or fragment to the C5aR is detected or measured, either directly or indirectly, according to methods described herein or other suitable methods. A decrease in the amount of complex formed relative to a suitable control (e.g., in the absence of the agent to be tested) is indicative that the agent binds said receptor or variant. The composition comprising C5aR can be a membrane fraction of a cell bearing recombinant C5aR protein or ligand binding variant thereof. The antibody or fragment thereof can be labeled with a label such as a radioisotope, spin label, antigen or epitope label, enzyme label, fluorescent group and chemiluminescent group.

Models of Inflammation

In vivo models of inflammation are available which can be used to assess the effects of antibodies and fragments of the invention in vivo as therapeutic agents. For example, leukocyte infiltration upon intradermal injection of a chemokine and an antibody or fragment thereof reactive with C5aR into a suitable animal, such as rabbit, mouse, rat, guinea pig or rhesus macaque can be monitored (see e.g., Van Damme, J. et al., J. Exp. Med., 176: 59-65 (1992); Zachariae, C. O. C. et al., J. Exp. Med. 171: 2177-2182 (1990); Jose, P. J. et al., J. Exp. Med. 179: 881-887 (1994)). In one embodiment, skin biopsies are assessed histologically for infiltration of leukocytes (e.g., eosinophils, granulocytes). In another embodiment, labeled cells (e.g., stably transfected cells expressing C5aR) capable of chemotaxis and extravasation are administered to the animal. An antibody or fragment to be assessed can be administered, either before, simultaneously with or after the labeled cells are administered to the test animal. A decrease of the extent of infiltration in the presence of antibody as compared with the extent of infiltration in the absence of inhibitor is indicative of inhibition.

Diagnostic and Therapeutic Applications

The antibodies and fragments of the present invention are useful in a variety of applications, including research, diagnostic and therapeutic applications. In one embodiment, the antibodies are labeled with a suitable label (e.g., fluorescent label, chemiluminescent label, isotope label, antigen or epitope label or enzyme label). For instance, they can be used to isolate and/or purify receptor or portions thereof and to study receptor structure (e.g., conformation) and function.

In addition, the various antibodies of the present invention can be used to detect C5aR or to measure the expression of receptor, for example, on T cells (e.g., CD8+ cells, CD45RO+ cells), monocytes and/or on cells transfected with a receptor gene. Thus, they also have utility in applications such as cell sorting (e.g., flow cytometry, fluorescence activated cell sorting), for diagnostic or research purposes.

The anti-C5aR antibodies of the present invention have value in diagnostic applications. Typically, diagnostic assays entail detecting the formation of a complex resulting from the binding of an antibody or fragment thereof to C5aR. For diagnostic purposes, the antibodies or antigen-binding fragments can be labeled or unlabeled. The antibodies or fragments can be directly labeled. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654 and 4,098,876). Immunohistochemistry of tissue samples may also be used in the diagnostic methods of the present invention. When unlabeled, the antibodies or fragments can be detected using suitable means, as in agglutination assays, for example. Unlabeled antibodies or fragments can also be used in combination with another (i.e., one or more) suitable reagent which can be used to detect antibody, such as a labeled antibody (e.g., a second antibody) reactive with the first antibody (e.g., anti-idiotype antibodies or other antibodies that are specific for the unlabeled immunoglobulin) or other suitable reagent (e.g., labeled protein A).

Kits for use in detecting the presence of a C5aR protein in a biological sample can also be prepared. Such kits will include an antibody or functional fragment thereof which binds to C5aR, as well as one or more ancillary reagents suitable for detecting the presence of a complex between the antibody or fragment and C5aR. The antibody compositions of the present invention can be provided in lyophilized form, either alone or in combination with additional antibodies specific for other epitopes. The antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the antibodies can be provided as a lyophilized mixture with the adjunct ingredients, or the adjunct ingredients can be separately provided for combination by the user. Generally these adjunct materials will be present in less than about 5% weight based on the amount of active antibody, and usually will be present in a total amount of at least about 0.001% weight based on antibody concentration. Where a second antibody capable of binding to the monoclonal antibody is employed, such antibody can be provided in the kit, for instance in a separate vial or container. The second antibody, if present, is typically labeled, and can be formulated in an analogous manner with the antibody formulations described above.

Similarly, the present invention also relates to a method of detecting and/or quantitating expression of C5aR by a cell, in which a composition comprising a cell or fraction thereof (e.g., membrane fraction) is contacted with an antibody or functional fragment thereof which binds to C5aR under conditions appropriate for binding of the antibody or fragment thereto, and binding is monitored. Detection of the antibody, indicative of the formation of a complex between antibody and C5aR, indicates the presence of the receptor. Binding of antibody to the cell can be determined as described above under the heading "Binding Assays", for example. The method can be used to detect expression of C5aR on cells from an individual (e.g., in a sample, such as a body fluid, such as blood, saliva or other suitable sample). The level of expression of C5aR on the surface of T cells or monocytes can also be determined, for instance, by flow cytometry, and the level of expression (e.g., staining intensity) can be correlated with disease susceptibility, progression or risk.

Chemoattractant receptors function in the migration of leukocytes throughout the body, particularly to inflammatory sites. Inflammatory cell emigration from the vasculature is regulated by a three-step process involving interactions of leukocyte and endothelial cell adhesion proteins and cell specific chemoattractants and activating factors (Springer, T. A, Cell, 76:301-314 (1994); Butcher, E. C., Cell, 67:1033-1036 (1991); Butcher, E. C. and Picker, L. J., Science (Wash. D.C.), 272:60-66 (1996)). These are: (a) a low affinity interaction between leukocyte selecting and endothelial cell carbohydrates; (b) a high-affinity interaction between leukocyte chemoattractant receptors and chemoattractant/activating factors; and (c) a tight-binding between leukocyte integrins and endothelial cell adhesion proteins of the immunoglobulin superfamily. Different leukocyte subsets express different repertoires of selectins, chemoattractant receptors and integrins. Additionally, inflammation alters the expression of endothelial adhesion proteins and the expression of chemoattractant and leukocyte activating factors. As a consequence, there is a great deal of diversity for regulating the selectivity of leukocyte recruitment to extravascular sites. The second step is crucial in that the activation of the leukocyte chemoattractant receptors is thought to cause the transition from the selectin-mediated cell rolling to the integrin-mediated tight binding. This results in the leukocyte being ready to transmigrate to perivascular sites. The chemoattractant/chemoattractant receptor interaction is also crucial for transendothelial migration and localization within a tissue (Campbell, J. J., et al., J. Cell Biol., 134:255-266 (1996); Carr, M. W., et al., Immunity, 4:179 187 (1996)). This migration is directed by a concentration gradient of chemoattractant leading towards the inflammatory focus.

C5aR has an important role in leukocyte trafficking. It is likely that C5aR is a key chemoattractant receptor for neutrophil, eosinophil, T cell or T cell subset or monocyte migration to certain inflammatory sites, and so anti-C5aR mAbs can be used to inhibit (reduce or prevent) leukocyte migration, particularly that associated with neutrophil tissue injury such as reperfusion injury and stroke, T cell dysfunction, such as autoimmune disease, or allergic reactions or with monocyte-mediated disorders such as atherosclerosis.

Accordingly, the antibodies and fragments thereof of the present invention can also be used to modulate receptor function in research and therapeutic applications. For instance, the antibodies and functional fragments described herein can act as inhibitors to inhibit (reduce or prevent) (a) binding (e.g., of a ligand, an inhibitor or a promoter) to the receptor, (b) a receptor signaling function, and/or (c) a stimulatory function. Antibodies which act as inhibitors of receptor function can block ligand or promoter binding directly or indirectly (e.g., by causing a conformational change). For example, antibodies can inhibit receptor function by inhibiting binding of a ligand, or by desensitization (with or without inhibition of binding of a ligand). Antibodies which bind receptor can also act as agonists of receptor function, triggering or stimulating a receptor function, such as a signaling and/or a stimulatory function of a receptor (e.g., leukocyte trafficking) upon binding to receptor.

Thus, the present invention provides a method of inhibiting leukocyte trafficking in a mammal (e.g., a human patient), comprising administering to the mammal an effective amount of an antibody or functional fragment of the present invention. The present invention also provides a method of inhibiting other effects associated with C5aR activity such as histamine release from basophils and granule release from eosinophils, basophils and neutrophils. Administration of an antibody or fragment of the present invention can result in amelioration or elimination of the disease state.

The monoclonal antibodies can also be used immunotherapeutically for immunopathological associated disease. The term "immunotherapeutically" or "immunotherapy" as used herein in conjunction with the monoclonal antibodies of the invention denotes both prophylactic as well as therapeutic administration. Thus, the monoclonal antibodies can be administered to high-risk patients in order to lessen the likelihood and/or severity of immunopathological disease or administered to patients already evidencing active disease, for example sepsis due to gram-negative bacterial infection.

The antibodies or functional fragments thereof can be used to treat allergy, atherogenesis, anaphylaxis, malignancy, chronic and acute inflammation, histamine and IgE-mediated allergic reactions, shock, and rheumatoid arthritis, atherosclerosis, multiple sclerosis, allograft rejection, fibrotic disease, asthma, inflammatory glomerulopathies or any immune complex related disorder.

Diseases or conditions of humans or other species which can be treated with inhibitors of C5aR receptor function (including antibodies or suitable fragments thereof), include, but are not limited to:

(a) inflammatory or allergic diseases and conditions, including respiratory allergic diseases such as asthma, allergic rhinitis, hypersensitivity lung diseases, hypersensitivity pneumonitis, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); anaphylaxis or hypersensitivity responses, drug allergies (e.g., to penicillin, cephalosporins), insect sting allergies; inflammatory bowel diseases, such as Crohn's disease and ulcerative colitis; spondyloarthropathies; scleroderma; psoriasis and inflammatory dermatoses such as dermatitis, eczema, atopic dermatitis, allergic contact dermatitis, urticaria; vasculitis (e.g., necrotizing, cutaneous, and hypersensitivity vasculitis);

(b) autoimmune diseases, such as arthritis (e.g., rheumatoid arthritis, psoriatic arthritis), multiple sclerosis, systemic lupus erythematosus, myasthenia gravis, juvenile onset diabetes, nephritides such as glomerulonephritis, autoimmune thyroiditis, Behcet's disease;

(c) graft rejection (e.g., in transplantation), including allograft rejection or graft-versus-host disease;

(d) atherosclerosis;

(e) cancers with leukocyte infiltration of the skin or organs;

(f) other diseases or conditions (including C5aR-mediated diseases or conditions), in which undesirable inflammatory responses are to be inhibited can be treated, including, but not limited to, reperfusion injury, stroke, adult respiratory distress syndrome, certain hematologic malignancies, cytokine-induced toxicity (e.g., septic shock, endotoxic shock), polymyositis, dermatomyositis, pemphigoid, Alzheimers Disease and granulomatous diseases including sarcoidosis.

Anti-C5aR antibodies of the present invention can block the binding of one or more ligands, thereby blocking the downstream cascade of one or more events leading to the above disorders.

In a preferred embodiment, the antibodies of the present invention are used in the treatment of sepsis, stroke or adult respiratory distress syndrome.

Diseases or conditions of humans or other species which can be treated with promoters of C5aR function (including antibodies or fragments thereof), include, but are not limited to immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; and immunosuppression due congenital deficiency in receptor function or other causes.

Modes of Administration

A immunotherapeutic method in accordance with this invention entails the administration of a therapeutic agent of the invention by injection or infusion prior to (prophylaxis) or following (therapy) the onset of the immunopathological disease.

One or more antibodies or fragments of the present invention can be administered to an individual by an appropriate route, either alone or in combination with (before, simultaneous with, or after) another drug or agent. For example, the antibodies of the present invention can also be used in combination with other monoclonal or polyclonal antibodies (e.g., in combination with antibodies which bind chemokine receptors, including, but not limited to, CCR2 and CCR3) or with anti-TNF or other anti-inflammatory agents or with existing blood plasma products, such as commercially available gamma globulin and immune globulin products used in prophylactic or therapeutic treatments. The antibodies or fragments of the present invention can be used as separately administered compositions given in conjunction with antibiotics and/or antimicrobial agents.

An effective amount of an antibody or fragment (i.e., one or more antibodies or fragments) is administered. An effective amount is an amount sufficient to achieve the desired therapeutic (including prophylactic) effect, under the conditions of administration, such as an amount sufficient for inhibition of a C5aR function, and thereby, inhibition of an inflammatory response.

A variety of routes of administration are possible including, but not necessarily limited to, oral, dietary, topical, parenteral (e.g., intravenous, intraarterial, intramuscular, subcutaneous injection), inhalation (e.g., intrabronchial, intraocular, intranasal or oral inhalation, intranasal drops), depending on the disease or condition to be treated. Other suitable methods of administration can also include rechargeable or biodegradable devices and slow release polymeric devices. The pharmaceutical compositions of this invention can also be administered as part of a combinatorial therapy with other agents.

Formulation of an antibody or fragment to be administered will vary according to the route of administration and formulation (e.g., solution, emulsion, capsule) selected. An appropriate pharmaceutical composition comprising an antibody or functional fragment thereof to be administered can be prepared in a physiologically acceptable vehicle or carrier. A mixture of antibodies and/or fragments can also be used. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, Remington's Pharmaceutical Science, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The antibodies and fragments of this invention can be lyophilized for storage and reconstituted in a suitable carrier prior to use according to art-known lyophilization and reconstitution techniques. The optimum concentration of the active ingredient(s) in the chosen medium can be determined empirically, according to procedures well known to the skilled artisan, and will depend on the ultimate pharmaceutical formulation desired. For inhalation, the antibody or fragment can be solubilized and loaded into a suitable dispenser for administration (e.g., an atomizer, nebulizer or pressurized aerosol dispenser).

The dosage ranges for the administration of the monoclonal antibodies of the invention are those large enough to produce the desired effect in which the symptoms of the immunopathological disease are ameliorated or the likelihood of infection or over stimulation of the immune system decreased. The dosage should not be so large as to cause adverse side effects, such as hyper-viscosity syndromes, pulmonary edema, conjestive heart failure, and the like. Generally, the dosage will vary with the age, condition, sex and extent of the disease in the patient and can be determined by one of skill in the art. The dosage can be adjusted by the individual physician in the event of anycomplication. Dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

It will be appreciated by those skilled in the art that the antibodies of the present invention may be introduced into a subject by administering a nucleic acid molecule comprising a sequence encoding the antibody. The nucleic acid molecule may be in the form of DNA or RNA or a chimeric molecule comprising both DNA or RNA. A nucleotide sequence encoding the antibody may be cloned into an expression vector where the sequence encoding the agent is operably linked with expression control elements. Expression control elements are well known in the art and include, for example, promoters, enhancers and appropriate start and stop codons.

A variety of methods can be used for introducing a nucleic acid encoding the antibody into a target cell in vivo. For example, the naked nucleic acid may be injected at the target site, may be encapsulated into liposomes, or may be introduced by way of a viral vector.

Direct injection of a nucleic acid molecule alone or encapsulated, for example, in cationic liposomes may be used for stable gene transfer of a nucleic acid encoding TSP-1 into non-dividing or dividing cells in vivo (Ulmer et al., Science 259:1745-1748 (1993)). In addition, the nucleic acid can be transferred into a variety of tissues in vivo using the particle bombardment method (Williams et al., Proc. Natl. Acad. Sci. USA 88:2726-2730 (1991)).

Viral vectors are useful for gene transfer of a nucleic acid molecules encoding the antibody into a specific cell type in vivo. Viruses are specialized infectious agents that can infect and propagate in specific cell types. This specificity for infecting particular cell types is especially suitable for targeting the antibody to selected cells in vivo. The selection of a viral vector will depend, in part, on the cell type to be targeted.

Specialized viral vectors are well known in the art that can target to specific cell types. Such vectors include, for example, recombinant adeno-associated viral vectors having general or tissue-specific promoters (Lebkowski et al. U.S. Pat. No. 5,354,678). Recombinant adeno-associated viral vectors have the added advantage that the recombinant virus can stably integrate into the chromatin of even quiescent non-proliferating cells (Lebkowski et al., Mol. Cell. Biol. 8:3988-3996 (1988)).

Viral vectors can be constructed to further control the type of cell that expresses the encoded antibody by incorporating a tissue-specific promoter or enhancer into the vector (Dai et al., Proc. Natl. Acad. Sci. USA 89:10892-10895 (1992)).

Retroviral vectors are also suitable for the methods for delivering nucleic acid molecules encoding the antibody in vivo. Such vectors can be constructed either to function as infectious particles or as non-infectious particles that undergo only a single initial round of infection.

Receptor-mediated DNA delivery approaches also can be used to deliver a nucleic acid molecule encoding the antibody into a cell in a tissue-specific manner using a tissue-specific ligand or an antibody that is non-covalently complexed with the nucleic acid molecule via a bridging molecule (Curiel et al., Hum. Gene Ther. 3:147-154 (1992); Wu and Wu, J. Biol. Chem. 262:4429-4432 (1987)).

Gene transfer to obtain expression of the antibody in a subject also can be performed by, for example, ex vivo transfection of autologous cells. Suitable cells for such ex vivo transfection include blood cells since these cells are readily accessible for manipulation and reintroduction back into the subject by methods well known in the art.

Gene transfer through transfection of cells ex vivo can be performed by a variety of methods, including, for example, calcium phosphate precipitation, diethyaminoethyl dextran, electroporation, lipofection, or viral infection. Such methods are well known in the art (see, for example, Sambrook et al., Molecular Cloning: A Laboratory Manual, Cold Springs Harbour Laboratory Press (1989)). Once the cells are transfected, they are then transplanted or grafted back into a subject to be treated. The cells once introduced into the body can produce the antibody, which can enter the circulation and inhibit platelet aggregation at the site of the disease or condition.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

The present invention will now be illustrated by the following Examples, which are not intended to be limiting in any way. The teachings of all references cited herein are incorporated herein by reference.

EXPERIMENTAL SECTION

Materials and Methods
1. Monoclonal Antibody Production and Flow Cytometry.

Monoclonal antibodies (MAbs) reactive with C5aR were generated by immunising C57BL/6 mice with $10^7$ L1.2 C5aR transfected cells [8], intraperitoneally, five to six times at 2-wk intervals. The final immunisation was injected intravenously. Four days later, the spleen was removed and cells were fused with the SP2/0 cell line as described [9]. MAbs reactive with C5aR were identified using C5aR transfected L1.2 cells, and untransfected L1.2 cells, or L1.2 cells transfected with unrelated receptors such as CXCR2 or CX3CR1 (V28) using immunofluorescent staining and analysis using a FACScan® (Becton Dickinson & Co., Mountain View, Calif.). MAb staining of cells was performed using standard procedures, as described previously [10].

2. Ligand Binding Assay

Recombinant human C5a was obtained from Sigma Chemical Co. (St. Louis, Mo.). $^{125}$I-Bolton-Hunter-labelled complement C5a was purchased from NEN-Dupont (Boston, Mass.), with a specific activity of 2200 Ci/mM. C5a binding to L1.2 C5aR transfectants was carried out as described previously [9, 11]. Briefly, cells were washed once in PBS and resuspended in binding buffer (50 mM Hepes, pH 7.5, 1 mM CaCl, 5 mM $MgCl_2$, 0.5% BSA and 0.05% azide) at a concentration of $10^7$/ml. Aliquots of 50 ml ($5 \times 10^5$ cells) were dispensed into microfuge tubes, followed by the addition of cold competitor and 1 nM of radiolabelled C5a. The final reaction volume was 200 µl. After a 60-min incubation at room temperature, the cells were washed three times with 1 ml of binding buffer containing 0.5 M NaCl. Cell pellets were then counted. Background binding was obtained by incubating cells with radiolabelled C5a and at least 400-fold excess of unlabelled C5a. Duplicates were used throughout the experiments and the standard deviations were always <10% of the mean.

3. Transfectant Chemotaxis Assay

C5aR transfected L1.2 cells were spun down and washed in migration medium (MM=RPMI 1640, 0.5% BSA) and resuspended at $10^7$ cells/ml. Tissue culture inserts (Becton Dickinson & Co., Mountain View, Calif.) were placed in each of the wells of 24-well tissue-culture plates, forming an upper and lower chamber separated by a polyethylene terephthalate membrane bearing 3-mm-diameter pores. Chemotactic C5a (diluted in assay medium) was added to 600 µl of assay medium in the 24-well tissue culture plates for a final concentration of 1 nM. One million cells in 100 µl were pre-incubated for 30 mins with the supernatants from the hybridomas containing the antibody. The cell-supernatant mixture or purified mAb was added to the upper chamber in the wells and the cells were allowed to migrate through to the lower chamber in an 5% $CO_2$, 37° C. incubator for 18 h. The inserts were removed after migration and the cells were counted by the FACScan®. Relative cell counts were obtained by acquiring events for a set time period of 30 seconds. This method was found to be highly reproducible, and enabled gating on the leukocytes and the exclusion of debris.

4. Neutrophil Chemotaxis Assays

Cell preparation: Neutrophils were isolated from peripheral blood by first obtaining the leucocyte fraction via a dextran sedimentation step for 40 min at room temperature. The cells were then layered onto Ficoll-Paque (Amersham Biosciences) for density gradient centrifugation at 2500 rpm for 15 min at room temperature. After hypotonic lysis of residual red blood cells, neutrophils were resuspended in equal volumes of RPMI 1640 (Invitrogen Inc.), M199 (Invitrogen Inc.) and 2% FCS (HyClone).

Chemotaxis Assay: Anti-C5aR MAbs, 6C12, 7F3 and 12D4 were added to neutrophils ($1 \times 10^7$/ml) at concentrations ranging from 0.5 to 10 ug/ml. The cells were then loaded into the upper chamber of 24-well inserts (Corning Inc., NY) with a polycarbonate membrane of 3.0 µm porosity and incubated for 10 min at room temperature. The inserts were then placed onto lower chambers containing human neutrophil chemoattractants such as C5a (0.1 to 100 nM) and IL-8 (both 1.12 ng/ml to 11.2 µg/ml). The neutrophils were then incubated for 30 min at 37° C. The number of neutrophils migrating through the membrane to the lower chamber were quantified by flow cytometry (FACSCalibur; BD Biosciences).

5. Competitive Inhibition Assay

Anti-C5aR MAbs were added at 50 ug/ml, to a C5aR N-terminal synthetically produced peptide (residues 9-29) known as "PEPI" (Biosource; Eldridge) at concentrations ranging from 1 to 100 µM. Mouse L1.2 cells transfected with human C5a receptor and resuspended in 1% bovine serine albumin (BSA; GibcoBRL) (1×107/ml) were then added to give a total volume of 100 µl. The cells were incubated for 30 min at 4° C. and washed once with 0.1% BSA. Fluorescein (FITC) conjugated, sheep anti-mouse IgG, F(ab')2 (Jackson Immunoresearch Laboratories Inc.) was used as a secondary Ab (1:200) and incubated for 15 min at 4° C., followed by an additional washing step with 0.1% BSA The cells were resuspended in 0.1% BSA and analysed by flow cytometry.

6. ELISA Assays

ELISAs were performed as described in Current Protocols in Immunology (Unit 2.1) (Edited by J. F. Coligan, A. M. Kruisbeek, D. B. Margulies, E. M. Shevach and W. Strober), John Wiley and Sons, New York. Briefly, 96-well flat bottom ELISA plates (Maxisorp; Nunc) were coated with 1 µg/ml protein (PEPI or OPG) in PBS at 37° C. for 1 hr, then blocked with BSA at 4° C. overnight. The plates were then washed, incubated with antibodies, washed and incubated with peroxidase-conjugated sheep anti-mouse IgG antibody. The substrate used was TMB substrate reagent (PharMingen).

Example 1

MAb Production and Flow Cytometry

L1.2 transfectants expressing high levels of C5aR [8] were used to immunize mice, and ten MAbs were identified via flow cytometry that reacted specifically with L1.2 cells transfected with C5aR, but not with L1.2 cells transfected with CX3CR1 (V28) or CXCR2. These ten MAbs were designated 12D4, 10G1, 5H11, 6C12, 10D4, 5F3, 7F3, 8D6, 11B9 and 1D12.

FIG. 1 is a set of histograms showing that MAb 7F3 reacts with C5aR transfectants (L1.2C5aR) and with human neutrophils but not with cells transfected with CX3CR1 (L1.2 V28) or with cells transfected with CXCR2 (L1.2CXCR2). These MAb 7F3 results are representative of the ten mAbs identified.

Example 2

Inhibition of C5a Binding to Cells Transfected with C5aR

Figure 2:
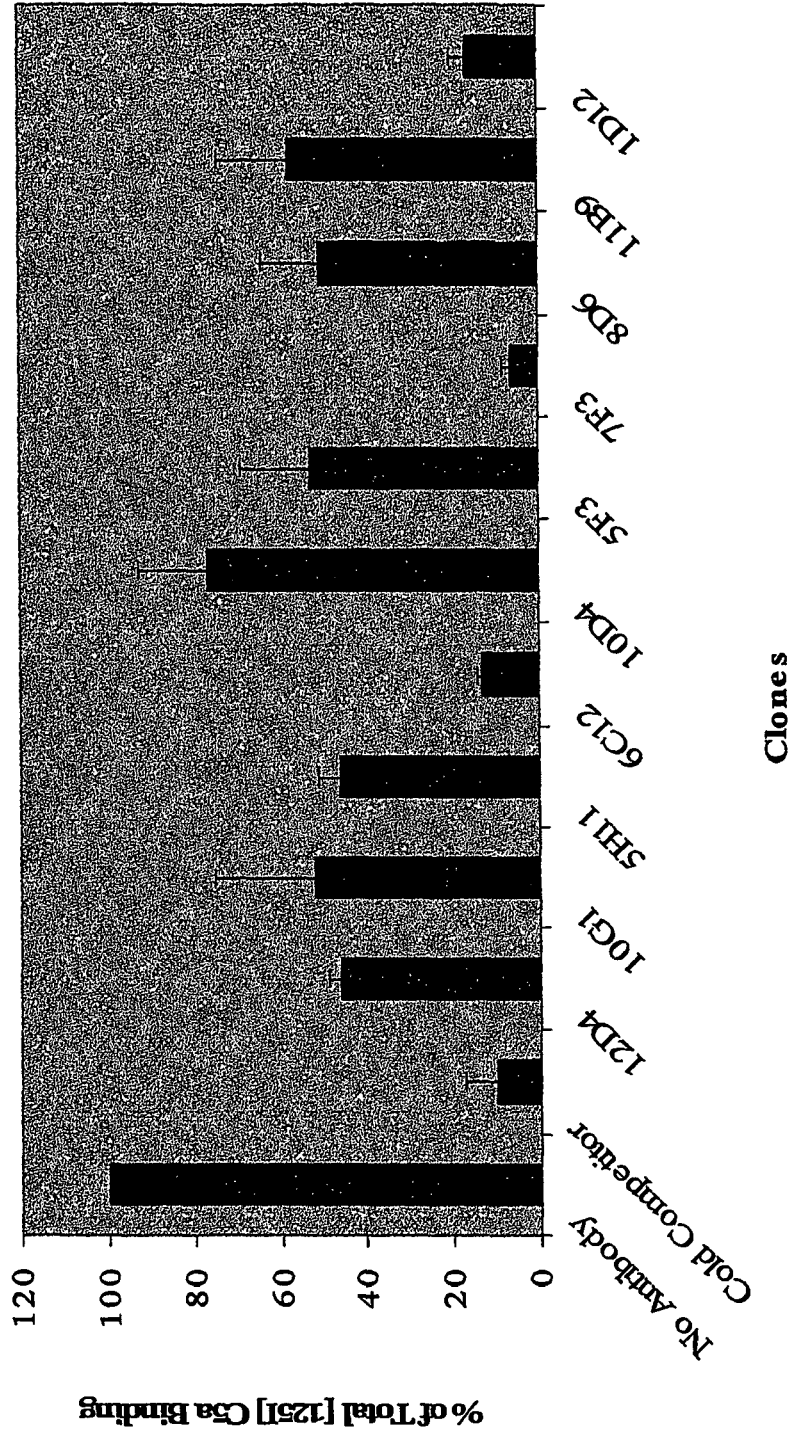
FIG. 2 shows the results of $^{125}$I C5a ligand binding assays involving a range of monoclonal antibodies including 7F3.
Figure 3:
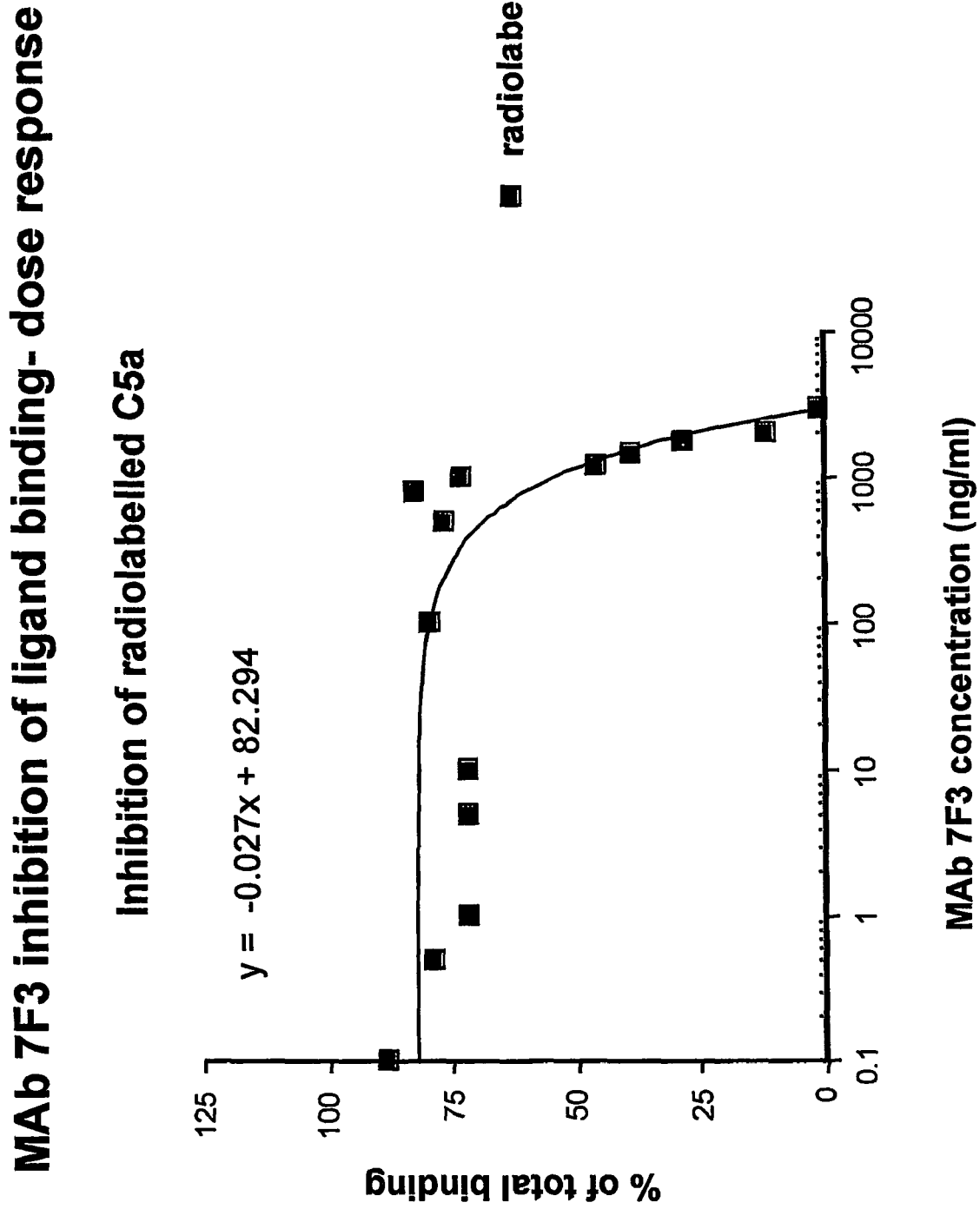
FIG. 3 shows the dose response inhibition of $^{125}$I C5a ligand binding by monoclonal antibody 7F3.

The ability of the MAbs to inhibit $^{125}$I-labelled C5a binding to C5aR transfectants was tested. FIG. 2 shows that MAb 7F3 completely inhibited binding of $^{125}$I-labelled C5a to the transfectants, and this inhibition was greater than that obtained with 400 nM cold C5a. This indicates that MAb 7F3 is able to completely block C5a binding to C5aR. MAbs 6C12 and 12D4 also showed substantial inhibition of $^{125}$I-labelled C5a binding to C5aR transfectants. Dose response inhibition of C5a binding to C5aR transfectants by MAb 7F3 is shown in FIG. 3.

Example 3

Inhibition of Human C5a Directed C5aR-Transfectant Migration by MAb 7F3

Figure 4:
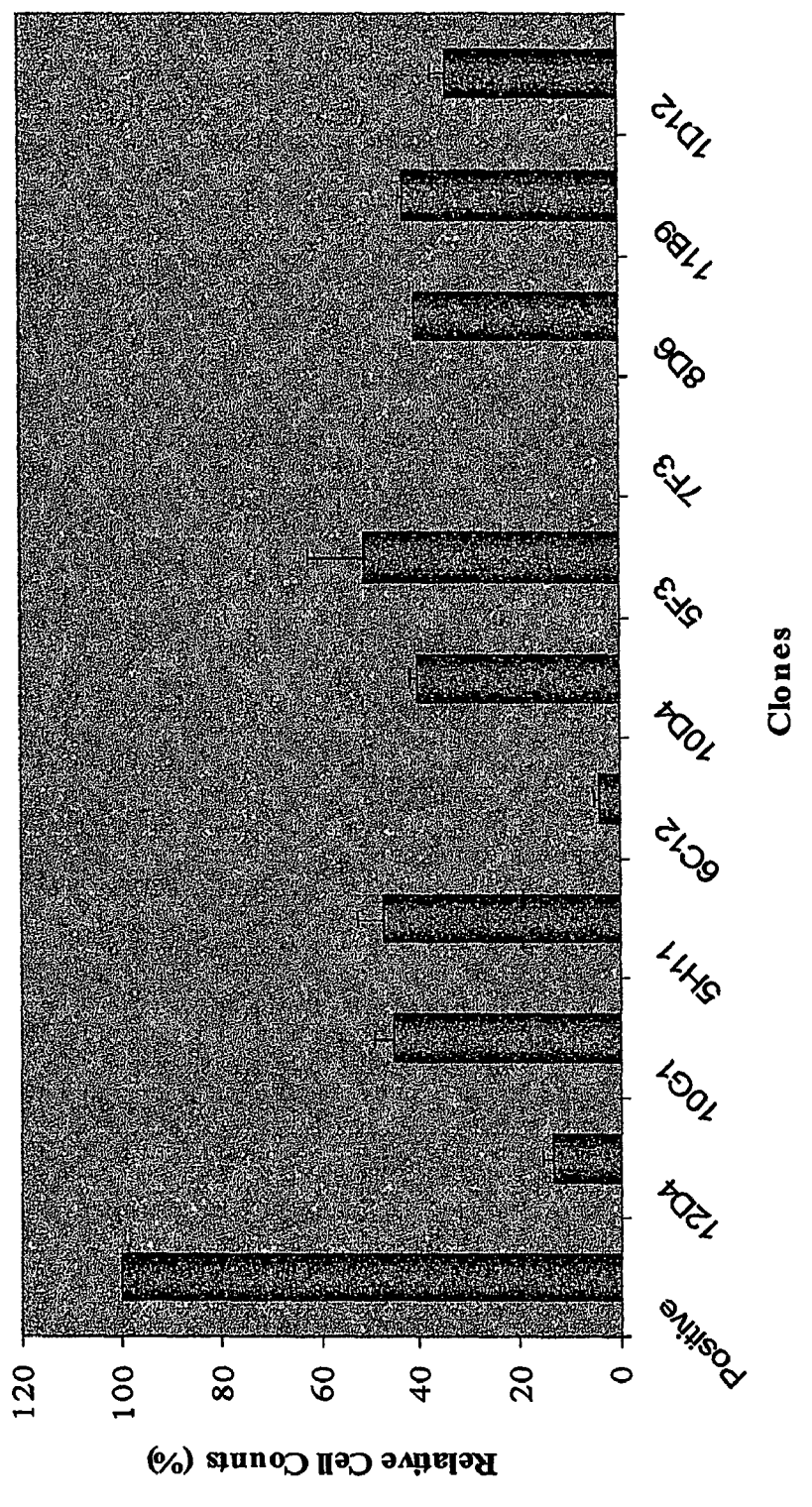
FIG. 4 shows the results of chemotaxis experiments performed using L1.2 cells transfected with C5aR and a range of monoclonal antibodies including 7F3, 6C12 and 12D4.
Figure 5:
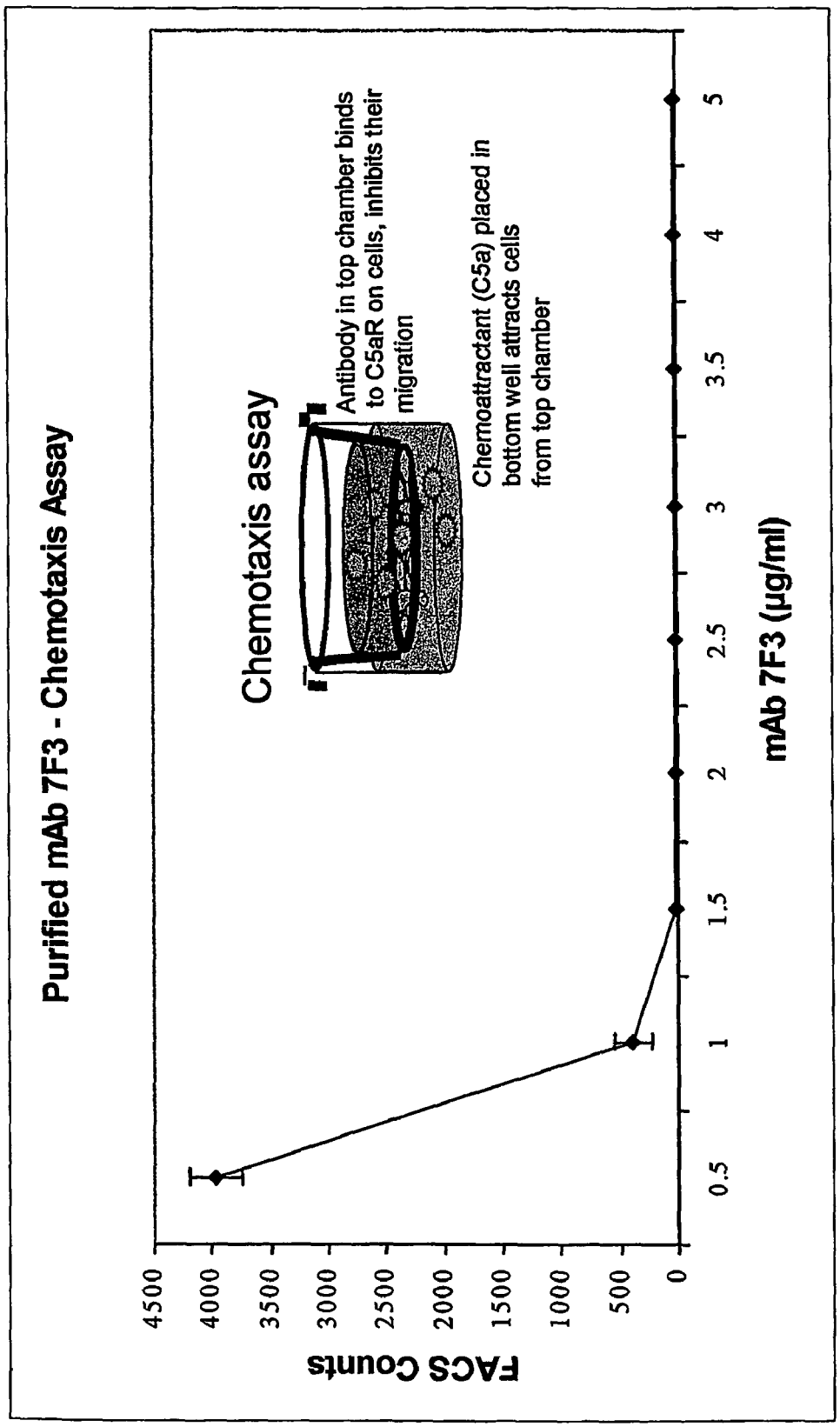
FIG. 5 shows the complete inhibition of L1.2 C5aR transfectant chemotaxis by monoclonal antibody 7F3.

Chemotaxis experiments were performed as described above using L1.2 cells transfected with C5aR. FIG. 4 shows that MAbs 7F3, 6C12 and 12D4 completely or substantially inhibited chemotaxis of the C5aR-L1.2 cells to C5a. FIG. 5 shows the dose response inhibition of chemotaxis of C5aR-L1.2 cells to C5a by mAb 7F3.

Example 4

Inhibition of Human C5a-Directed Neutrophil Migration by MAb 7F3

Anti-C5aR MAbs were dialysed in 1×PBS (GibcoBRL), and both the dialysed and non-dialysed 7F3 MAbs were added to neutrophils ($1 \times 10^7$/ml) at 5 ug/ml. Negative controls (no Ab addition, and 1×PBS added) were included. The cells were then loaded into the upper chamber of 24-well inserts (Corning Inc., NY) with a polycarbonate membrane of 3.0 µm porosity and incubated for 10 min at room temperature. The inserts were then placed onto lower chambers containing the human neutrophil chemoattractant C5a (0.1 to 100 nM). The neutrophils were then incubated for 30 min at 37° C. The number of neutrophils migrating through the membrane to the lower chamber were quantified by flow cytometry (FACSCalibur; BD Biosciences).

Figure 6:
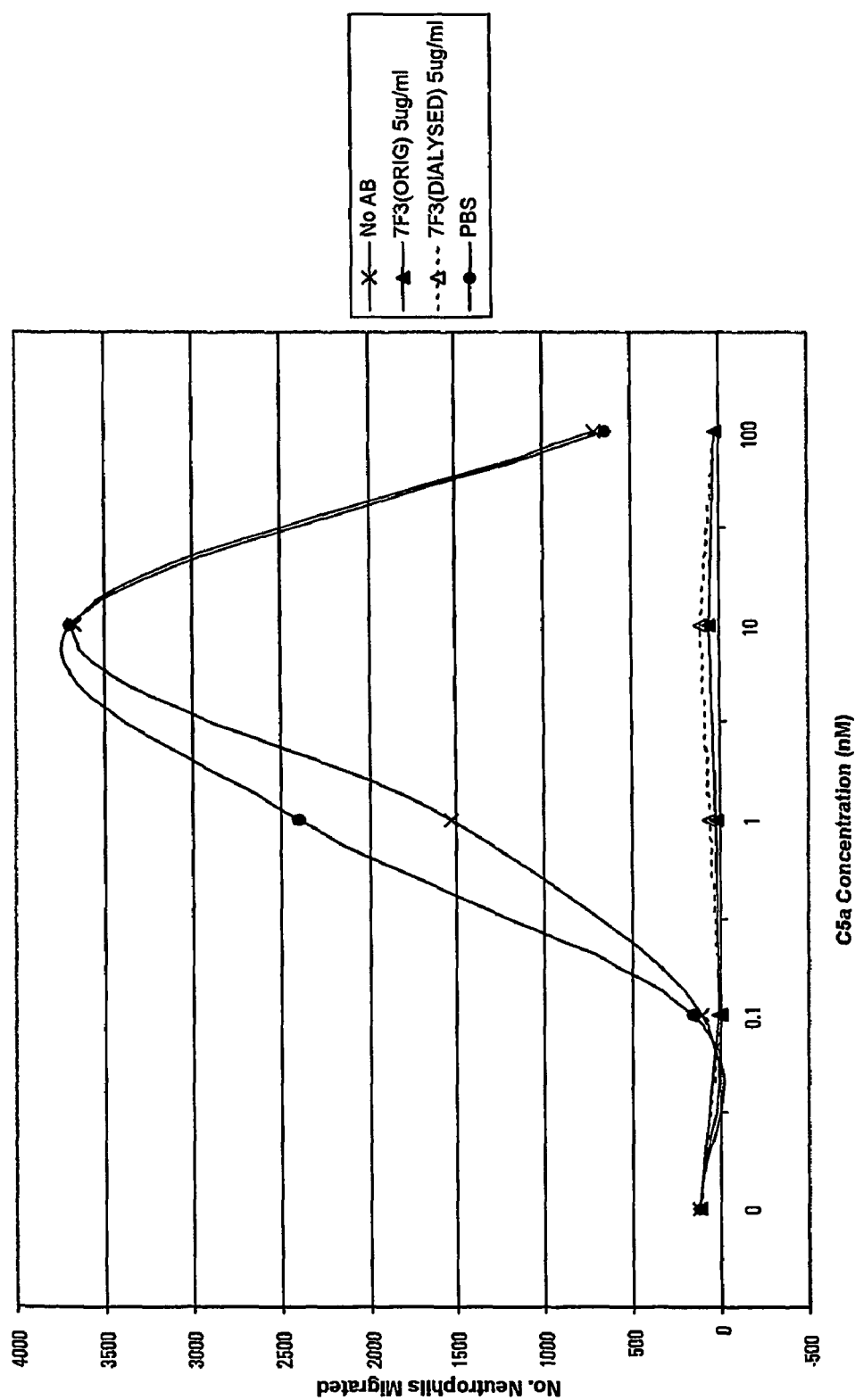
FIG. 6 shows the complete inhibition of C5a-directed neutrophil chemotaxis by monoclonal antibody 7F3.

FIG. 6 shows that addition of MAb 7F3 (whether dialysed or non-dialysed) resulted in inhibition of neutrophil migration compared to the two negative controls.

Example 5

Inhibition of Human C5a-Directed Neutrophil Migration by MAbs 7F3, 6C12 and 12D4

The three anti-C5aR MAbs, 7F3, 12D4 and 6C12 were added to neutrophils ($1 \times 10^7$/ml) at 5 ug/ml. Negative controls (no Ab addition, and 1×PBS added) were included. The cells were then loaded into the upper chamber of 24-well inserts (Corning Inc., NY) with a polycarbonate membrane of 3.0 µm porosity and incubated for 10 min at room temperature. The inserts were then placed onto lower chambers containing the human neutrophil chemoattractant C5a (1.12 to 1120 ng/ml). The neutrophils were then incubated for 30 min at 37° C. The number of neutrophils migrating through the membrane to the lower chamber were quantified by flow cytometry (FACSCalibur; BD Biosciences).

Figure 7:
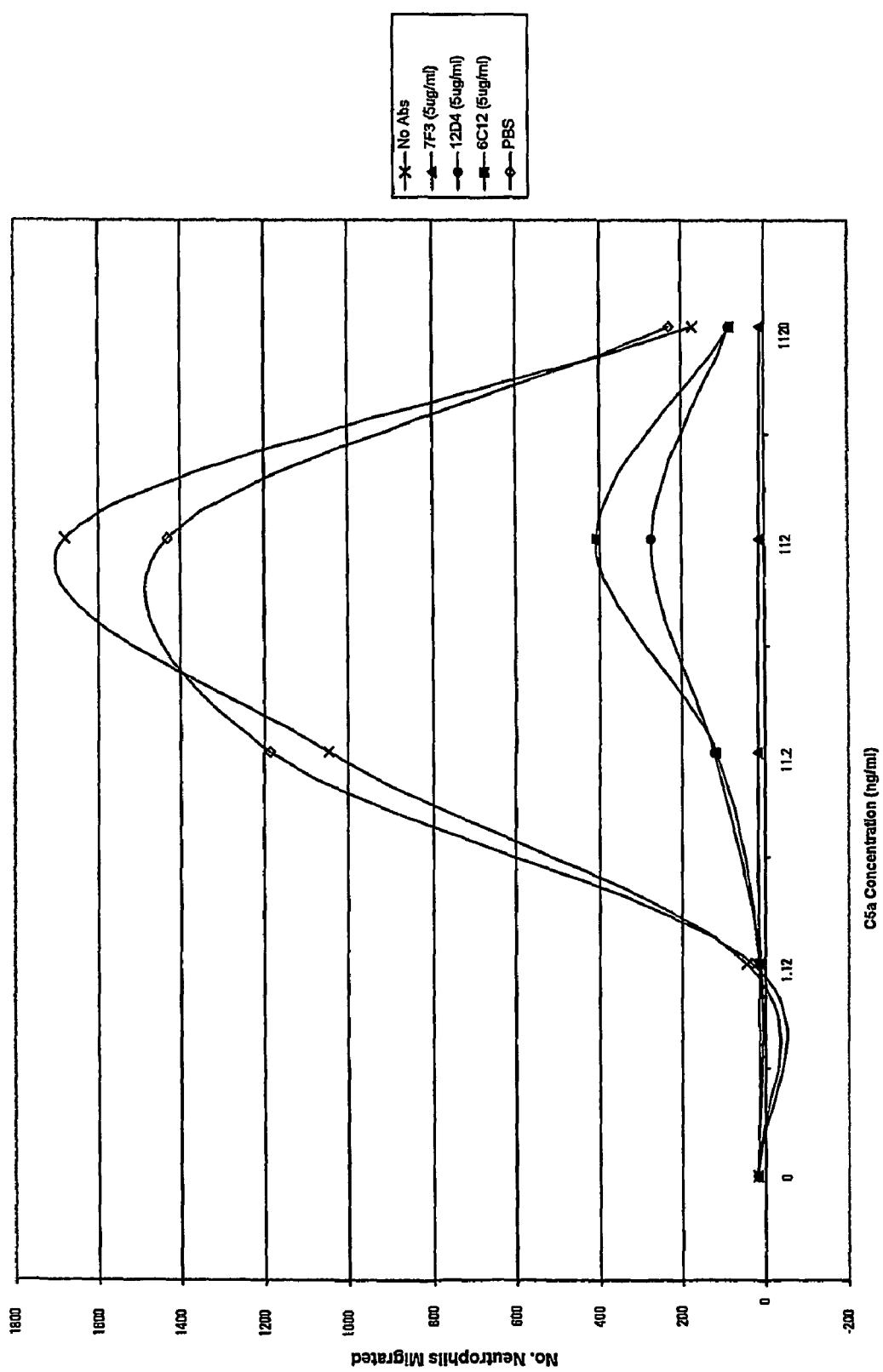
FIG. 7 shows inhibition of C5a-directed neutrophil chemotaxis by monoclonal antibodies 7F3, 6C12 and 12D4.

The results presented in FIG. 7 show that all three MAbs exhibited inhibition of neutrophil migration towards C5a compared to the two negative controls. In particular, the 7F3 MAb showed the most effective inhibition, resulting in a 140-fold reduction in neutrophil migration numbers to background levels.

Example 6

Inhibition of Human IL-8-Directed Neutrophil Migration by MAbs 7F3, 12D4 and 6C12

The three anti-C5aR MAbs, 7F3, 12D4 and 6C12; and the dialysed sample of 7F3 were added to purified neutrophils ($1 \times 10^7$/ml) at 5 ug/ml and loaded into the upper chamber of 24-well inserts. Negative controls (no Ab addition, and 1×PBS added) were again included. After 10 min incubation at room temperature. The inserts were then placed onto lower chambers containing IL-8 (1.12 to 1120 ng/ml), a human neutrophil chemoattractant that binds the CXCR1 and CXCR2 receptors expressed on the surface of neutrophils. The neutrophils were then incubated for 30 min at 37° C. The number of neutrophils migrating through the membrane to the lower chamber were quantified by flow cytometry (FACSCalibur; BD Biosciences).

Figure 8:
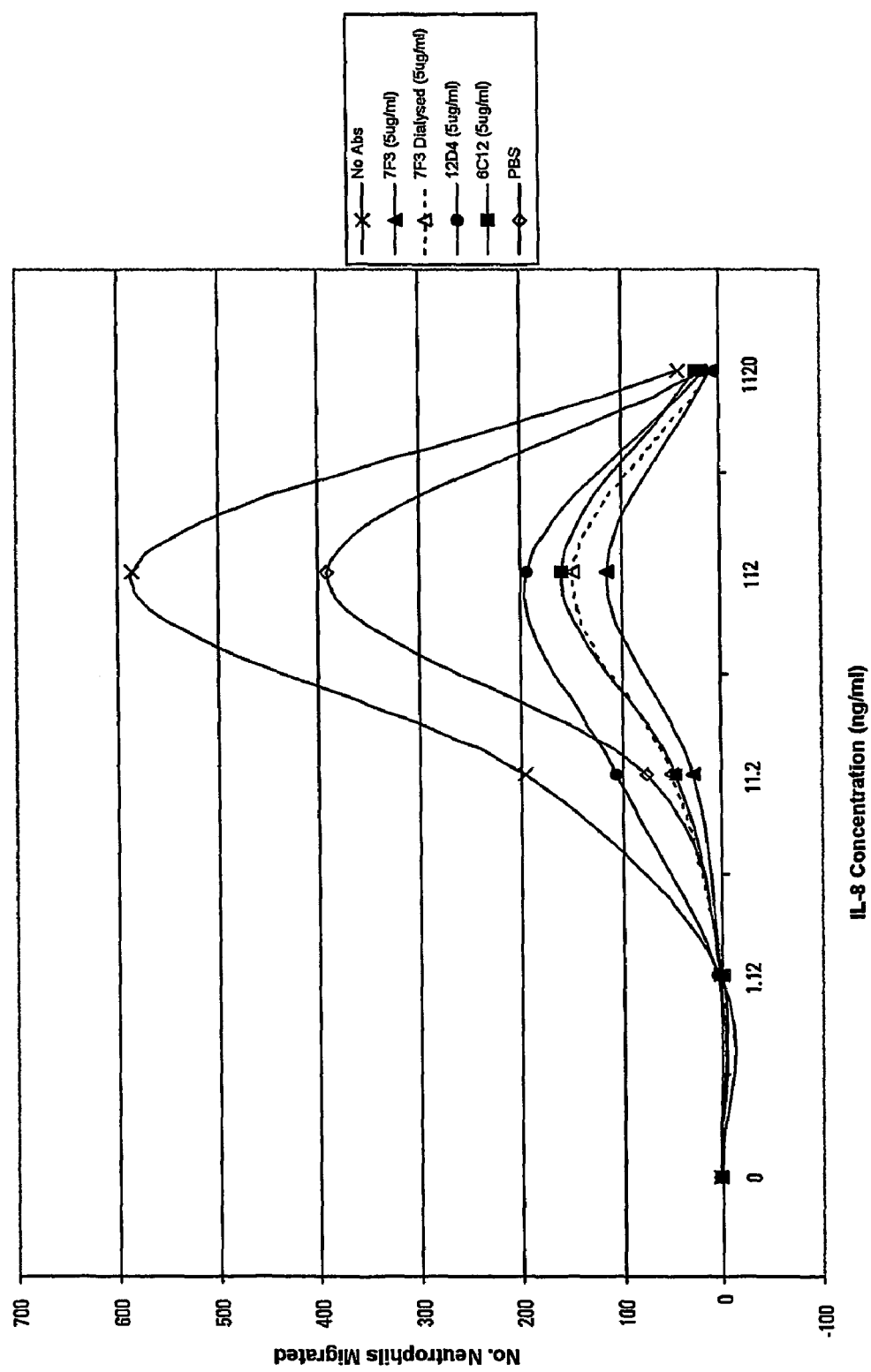
FIG. 8 shows inhibition of IL-8-directed neutrophil chemotaxis by monoclonal antibodies 7F3, 6C12 and 12D4.

FIG. 8 shows that all three MAbs exhibited inhibition of neutrophil migration towards IL-8. 7F3 MAb (both dialysed and non-dialysed) was the most effective inhibitor resulting in a 5-fold reduction in neutrophil migration numbers.

MAB 7F3 was also tested for its ability to inhibit other neutrophil chemoattractants, particularly CXCR1 and CXCR2 ligands. Table 1 shows substantial inhibition of neutrophil migration to a number of neutrophil chemoattractants, particularly CXCR1 and CXCR2 ligands, in neutrophil chemotaxis assays.

TABLE 1

| Chemoattractant (112 ng/ml) | % Inhibition |
|---|---|
| C5a | 98 |
| IL-8 | 81 |
| GCP-2 | 91 |
| ENA-78 | 83 |

Example 7

Competitive Inhibition of Binding of MAbs 7F3, 12D4 and 6C12 to C5aR Transfectants by a C5aR N-terminal Peptide (9-29)

Binding of the MAbs 7F3, 12D4 and 6C12 to cells transfected with C5aR was measured by staining with fluorescein (FITC) conjugated sheep anti-mouse IgG. The ability of a C5aR N-terminal peptide (residues 9-29) to inhibit this binding was then assessed according to the methodology described above. This C5aR N-terminal peptide has the sequence PDYGHYDDKDTLDLNTPVDKT and is referred to herein as "PEPI" (SEQ ID NO:35).

Figure 9A:
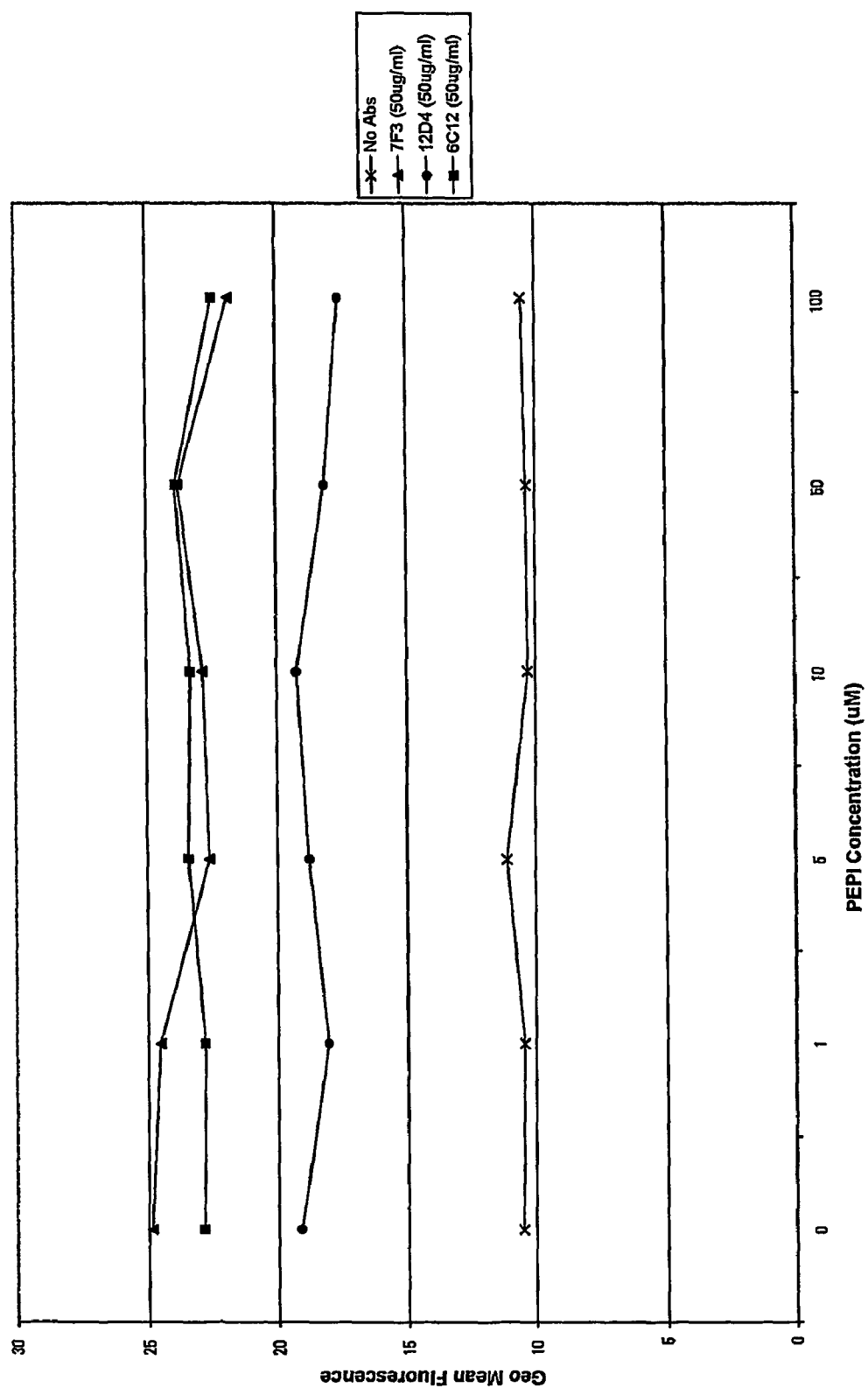
FIG. 9a presents results of an experiment to measure competitive inhibition of Anti-C5aR MAb binding to L1.2 cells transfected with human C5aR by the C5aR N-terminal peptide PEPI.

FIG. 9(a) shows that increasing concentrations of PEPI did not inhibit the fluorescence staining of the three anti-C5aR MAbs. The fluorescence staining remained stable, even at concentrations of PEPI of 100 μM.

Figure 9B:
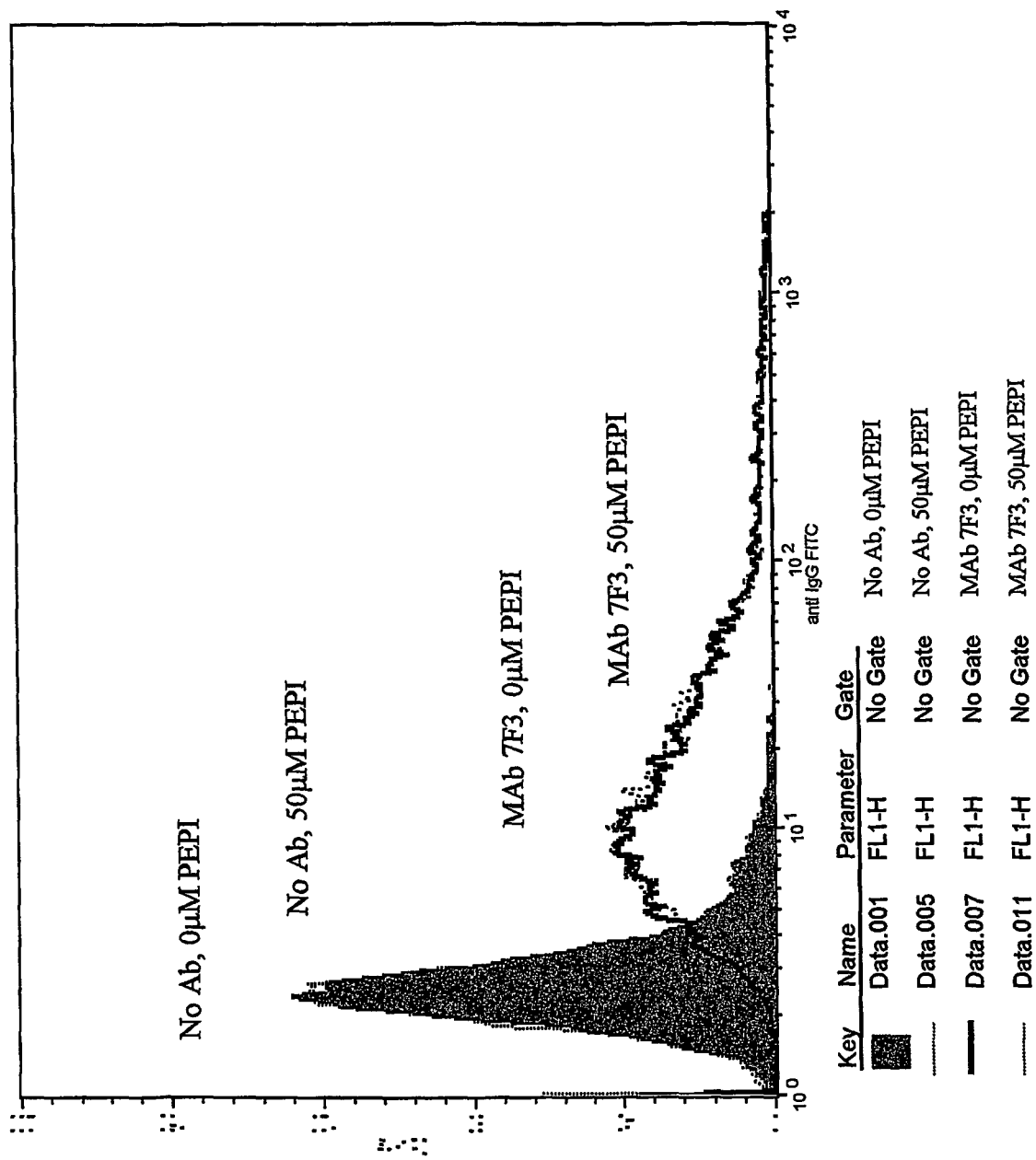
FIG. 9b presents results of an experiment measuring FACS staining of purified neutrophils with MAb 7F3 in the presence and absence of the C5aR N-terminal peptide PEPI.

FIG. 9(b) shows that PEPI (at a concentration of 50 μM) failed to inhibit FACS staining of purified neutrophils with MAb 7F3.

Example 8

Reactivity of MAbs 7F3, 12D4 and 6C12 with C5aR N-Terminal Peptide 9-29 ("PEPI") and OPG ELISA assays were performed as described above to measure the reactivity of MAbs 6C12, 12D4, 7F3, with PEPI and OPG. OPG is a member of the TNF-receptor superfamily which binds specifically to its ligand TNFSF11/OPGL. More specifically, OPG is an osteoblast-secreted decoy receptor that functions as a negative regulator of bone resorption.

MAbs 6C12, 12D4 and 7F3 were used in the ELISA as purified proteins at a concentration of 1 μg/mL. MAb 9C1 (which is specific for OPG) and MAb 11B9 (which recognises PEPI) were used as positive controls. These control MAbs were used in the form of undiluted tissue culture supernatant.

Figure 10:
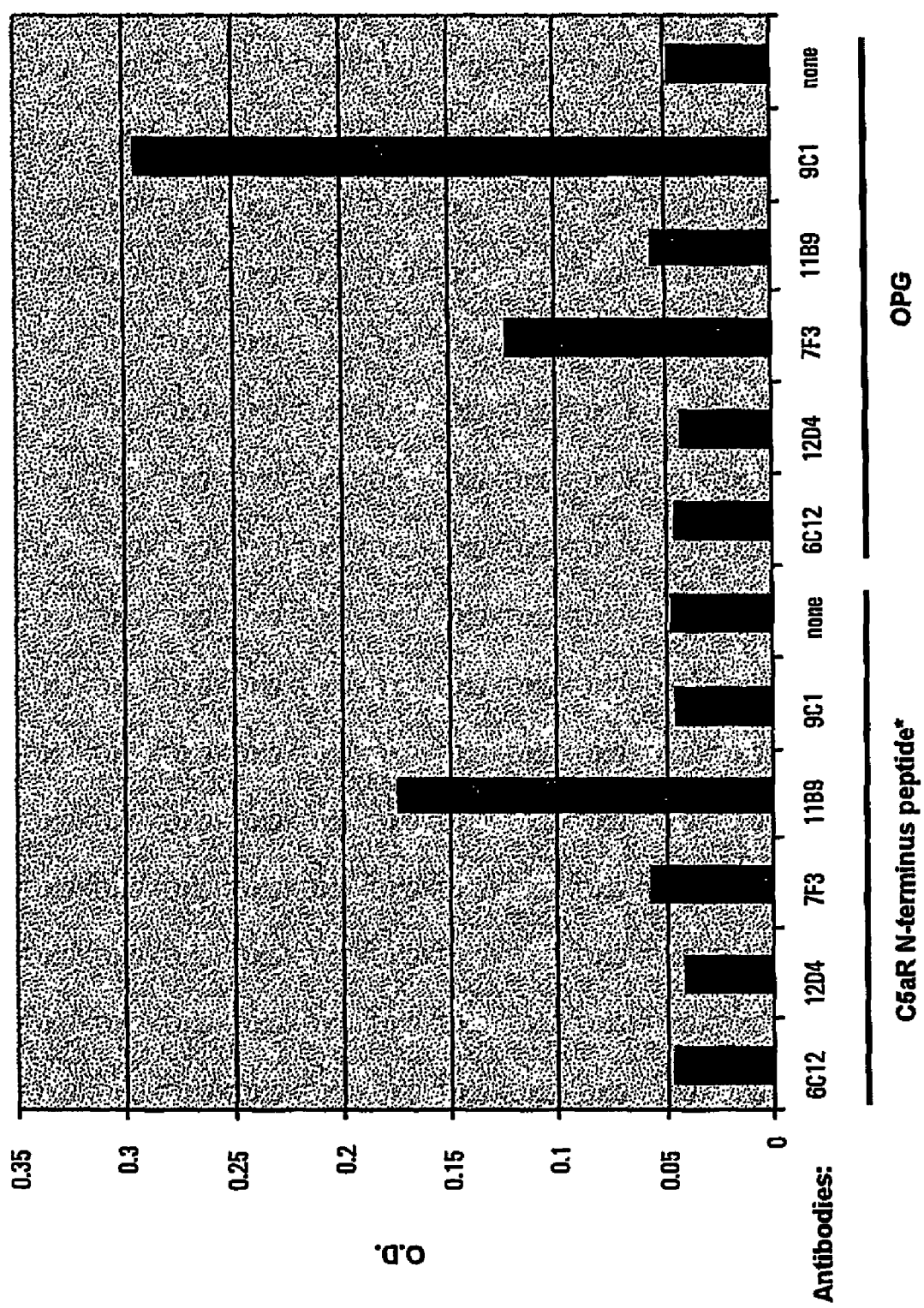
FIG. 10 presents results of an ELISA assay measuring reactivity of MAb 6C12, F3 and 12D4 to C5aR N-terminal 9-29 ("PEPI") and OPG.

FIG. 10 shows that MAbs 6C12, 12D4 and 7F3 were unreactive with PEPI. MAb 7F3 showed a small degree of cross-reactivity with OPG.

Example 9

Sequence Determination of Anti-C5aR MAbs 7F3, 12D4 and 6C12

The nucleotide sequence of anti-C5aR antibodies 7F3, 12D4 and 6C12 was determined from RNA extracted from antibody expressing hybridoma cells. To determine the primers used to amplify the variable regions of the heavy and light chains, the protein sequence of the variable region of the three antibodies was determined by Biogen Inc. and the isotype of the antibodies was determined using the Mouse Monoclonal Antibody isotyping kit—IsoStrip (Roche Cat. No. 1 493 027). Therefore, the 5' Framework 1 primer was derived from the Biogen Inc. protein sequence and the 3' primer was based on the isotype of the antibodies.

The isotype of each of the anti-C5aR antibodies is as follows:

6C12: light chain Kappa
6C12: heavy chain IgG3
7F3: light chain Kappa
7F3: heavy chain IgG2a
12D4: light chain Kappa
12D4: heavy chain IgG2b Total RNA was isolated from hybridoma cells using Trizol reagent (Invitrogen, Cat. No. 15596-018). RNA was isolated as described by the manufacturer. Briefly, approx. $5 \times 10^6$ cells were lysed in 1 ml of Trizol reagent. Cellular debris was cleared with 200 μl of chloroform and centrifugation. The aqueous RNA containing layer was removed and the RNA precipitated with 250 μl of isopropanol.

Total RNA (2 μg) was used to make cDNA using the AMV reverse transcriptase (Promega Cat. No. M5101). The cDNA was then used as template to amplify the variable region coding sequence using the following primers:

Primers for 6C12 Variable Light Chain:

```
mIgkapFI15':
    GATGTTTTGATGACCCAAACTCC        (SEQ ID NO: 2)

mIgkapcon3':
    ACACTCATTCCTGTTGAAGCTCTTG      (SEQ ID NO: 3)
```

Primers for 6C12 Variable Heavy Chain:

```
mIgVh2 5'
SAGGTCCAGCTGCARCAGTC  FR1 VhIIA family  (SEQ ID NO: 4)

mIgG3con3'
TGGGCATGAAGAACCTGG    Hinge region      (SEQ ID NO: 5)
```

Primers for 7F3 Variable Light Chain:

```
mIgkapFR15':
    GATGTTTTGATGACCCAAACTCC        (SEQ ID NO: 6)

mIgkapcon3':
    ACACTCATTCCTGTTGAAGCTCTTG      (SEQ ID NO: 7)
```

Primers for 7F3 Variable Heavy Chain:

```
mIgVh2 5':
SAGGTCCAGCTGCARCAGTC  FR1 VhIIA family  (SEQ ID NO: 8)

mIgG2acon3':
TTTGCATGGAGGACAGGG                      (SEQ ID NO: 9)
```

Primers for 12D4 Variable Light Chain:

```
mIgkapFR15':
    GATGTTTTGATGACCCAAACTCC        (SEQ ID NO: 10)

mIgkapcon3':
    ACACTCATTCCTGTTGAAGCTCTTG      (SEQ ID NO 11)
```

Primers for 12D4 Variable Heavy Chain:

```
mIgVh1 5':   CAGGTGCAGCTGAAGSAGTC   (SEQ ID NO: 12)
             FR1 VhIB family mIgG3con3':  TGGGCATGAAGAACCTGG     (SEQ ID NO: 13)
             Hinge region
```

Polymerase chain reaction (PCR) was performed using the high fidelity Pfu polymerase (Promega Cat. No. M7741) with an annealing temperature of 60° C. and primer extension at 72° C. for 3 min. The resulting PCR fragment of approx. 700 bp was cloned into pGEM-Teasy (Promega Cat. No. A1360). Single colonies were isolated and sequenced by a commercial sequencing facility (SUPAMAC).

The resultant sequences are provided herein as follows:

| | |
|---|---|
| 6C12 variable light chain (DNA) sequence: | SEQ ID NO:14 |
| 6C12 variable light chain (protein) sequence: | SEQ ID NO:15 |
| 6C12 variable heavy chain (DNA) sequence: | SEQ ID NO:16 |
| 6C12 variable heavy chain (protein) sequence: | SEQ ID NO:17 |
| 7F3 variable light chain (DNA) sequence: | SEQ ID NO:18 |
| 7F3 variable light chain (protein) sequence: | SEQ ID NO:19 |
| 7F3 variable heavy chain (DNA) sequence: | SEQ ID NO:20 |
| 7F3 variable heavy chain (protein) sequence: | SEQ ID NO:21 |
| 12D4 variable light chain (DNA) sequence: | SEQ ID NO:22 |
| 12D4 variable light chain (protein) sequence: | SEQ ID NO:23 |
| 12D4 variable heavy chain (DNA) sequence: | SEQ ID NO:24 |
| 12D4 variable heavy chain (protein) sequence: | SEQ ID NO:25 |

Example 10

Analysis of DNA and Protein Sequence Identity and Similarity for MAbs 7F3, 12D4 and 6C12

The three anti-C5aR antibodies (7F3, 12D4 and 6C12) DNA and protein sequence were compared using MacVector 6.5.3. The ClustalW(1.4) multiple alignment program was utilized for this analysis.

(i) Analysis of Variable Light Chain DNA Sequences:
Alignment of the variable light chain DNA sequences for 7F3, 12D4 and 6C12 is shown in FIG. 11.
Clustal W(1.4) multiple sequence alignment analysis yielded the following results:
3 Sequences Aligned. Alignment Score=6612
Gaps Inserted=0 Conserved Identities=315
Pairwise Aligmnent Mode: Slow
Pairwise Alignment Parameters:
Open Gap Penalty=10.0 Extend Gap Penalty=5.0
Multiple Alignment Parameters:
Open Gap Penalty=10.0 Extend Gap Penalty=5.0
Delay Divergent=40% Transitions: Weighted
Processing time: 0.4 seconds
1. 7F3 Vk vs. 6c12 Vk
Aligned Length=336 Gaps=0
Identities=320 (95%)
2. 7F3 Vk vs. 12d4 Vk
Aligned Length=336 Gaps=0
Identities=320 (95%)
3. 6c12 Vk vs. 12d4 Vk
Aligned Length=336 Gaps=0
Identities=326 (97%)

(ii) Analysis of Variable Heavy Chain DNA Sequence
Alignment of the variable heavy chain DNA sequences for 7F3, 12D4 and 6C12 is shown in FIG. 12.
Clustal W(1.4) multiple sequence alignment analysis yielded the following results:
3 Sequences Aligned. Alignment Score=5346
Gaps Inserted=3 Conserved Identities=200
Pairwise Alignment Mode: Slow
Pairwise Alignment Parameters:
Open Gap Penalty=10.0 Extend Gap Penalty=5.0
Multiple Alignment Parameters:
Open Gap Penalty=10.0 Extend Gap Penalty=5.0
Delay Divergent=40% Transitions: Weighted
Processing time: 0.5 seconds
1. 7F3 Vh vs. 6c12 Vh
Aligned Length=363 Gaps=0
Identities=333 (91%)
2. 7F3 Vh vs. 12d4 Vh
Aligned Length=363 Gaps=3
Identities=210 (57%)
3. 6c12 Vh vs. 12d4 Vh
Aligned Length=363 Gaps=3
Identities=210 (57%)

(iii) Analysis of Variable Light Chain Protein Sequence

Alignment of the variable light chain protein sequences for 7F3, 12D4 and 6C12 is shown in FIG. 13.

Clustal W(1.4) multiple sequence alignment analysis yielded the following results:
3 Sequences Aligned. Alignment Score=1902
Gaps Inserted=0 Conserved Identities=99
Pairwise Alignment Mode: Slow
Pairwise Alignment Parameters:
Open Gap Penalty=10.0 Extend Gap Penalty=0.1
Similarity Matrix: blosum
Multiple Alignment Parameters:
Open Gap Penalty=10.0 Extend Gap Penalty=0.1
Delay Divergent=40% Gap Distance=8
Similarity Matrix: blosum
Processing time: 0.1 seconds
1. 7F3 Vk vs. 6c12 Vk
Aligned Length=112 Gaps=0
Identities=102 (91%) Similarities=5 (4%)
2. 7F3 Vk vs. 12d4 Vk
Aligned Length=112 Gaps=0
Identities=103 (91%) Similarities=4 (3%)
3. 6c12 Vk vs. 12d4 Vk
Aligned Length=112 Gaps=0
Identities=104 (92%) Similarities=4 (3%)

(iv) Analysis of Variable Heavy Chain Protein Sequence

Alignment of the variable heavy chain protein sequences for 7F3, 12D4 and 6C12 is shown in FIG. 14.

Clustal W(1.4) multiple sequence alignment analysis yielded the following results:
3 Sequences Aligned. Alignment Score=1432
Gaps Inserted=2 Conserved Identities=51
Pairwise Alignment Mode: Slow
Pairwise Alignment Parameters:
Open Gap Penalty=10.0 Extend Gap Penalty=0.1
Similarity Matrix: blosum
Multiple Alignment Parameters:
Open Gap Penalty=10.0 Extend Gap Penalty=0.1
Delay Divergent=40% Gap Distance=8
Similarity Matrix: blosum
Processing time: 0.1 seconds
1. 7F3 Vh vs. 6c12 Vh
Aligned Length=121 Gaps=0
Identities=107 (88%) Similarities=6 (4%)
2. 7F3 Vh vs. 12d4 Vh
Aligned Length=121 Gaps=2
Identities=52 (42%) Similarities=25 (20%)
3. 6c12 Vh vs. 12d4 Vh
Aligned Length=121 Gaps=2
Identities=54 (44%) Similarities=25 (20%)

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Gerard, C. and N. P. Gerard, C5A anaphylatoxin and its seven transmembrane-segment receptor. Annual Review of Immunology, 1994. 12: p. 775-808.
2. Murdoch, C. and A. Finn, Chemokine receptors and their role in inflammation and infectious diseases. Blood, 2000. 95(10): p. 3032-43.
3. Watanabe, H., et al., Analysis of C5a receptor by monoclonal antibody. Journal of Immunological Methods, 1995. 185(1): p. 19-29.
4. Pellas, T. C., et al., Novel C5a receptor antagonists regulate neutrophil functions in vitro and in vivo. Journal of Immunology, 1998. 160(11): p. 5616-21.
5. Konteatis, Z. D., et al., Development of C5a receptor antagonists. Differential loss of functional responses. Journal of Immunology, 1994. 153(9): p. 4200-5.
6. Kaneko, Y., et al., Antagonistic peptides against human anaphylatoxin C5a. Immunology, 1995. 86(1): p. 149-54.
7. Morgan, E. L., et al., Anti-C5a receptor antibodies. Characterization of neutralizing antibodies specific for a peptide, C5aR-(9-29), derived from the predicted amino-terminal sequence of the human C5a receptor. Journal of Immunology, 1993. 151(1): p. 377-88.
8. Campbell, J. J., et al., Biology of chemokine and classical chemoattractant receptors: differential requirements for adhesion-triggering versus chemotactic responses in lymphoid cells. J Cell Biol, 1996. 134(1): p. 255-66.
9. Heath, H., et al., Chemokine receptor usage by human eosinophils. The importance of CCR3 demonstrated using an antagonistic monoclonal antibody. J Clin Invest, 1997. 99(2): p. 178-84.
10. Ponath, P. D., et al., Molecular cloning and characterization of a human eotaxin receptor expressed selectively on eosinophils [see comments]. J Exp Med, 1996. 183(6): p. 2437-48.
11. Ponath, P. D., et al., Cloning of the human eosinophil chemoattractant, eotaxin. Expression, receptor binding, and functional properties suggest a mechanism for the selective recruitment of eosinophils. J Clin Invest, 1996. 97(3): p. 604-12.

The invention claimed is:

1. An isolated antibody or a functional fragment thereof that is reactive with the second extracellular loop of C5aR set forth as the amino acid sequence from residue 175 to 206 of SEQ ID NO: 1, wherein the antibody or functional fragment thereof reduces or inhibits the binding of C5a to C5aR.

2. An isolated antibody or a functional fragment thereof that is reactive with the same epitope of C5aR as a monoclonal antibody as deposited with ECACC under accession number 00110609, wherein the antibody or functional fragment thereof reduces or inhibits the binding of C5a to C5aR.

3. An isolated antibody or a functional fragment thereof that is reactive with the same epitope of C5aR as a monoclonal antibody as deposited with ECACC under accession number 02090226, wherein the antibody or functional fragment thereof reduces or inhibits the binding of C5a to C5aR.

4. An isolated antibody or a functional fragment thereof that is reactive with the same epitope of C5aR as a monoclonal antibody as deposited with ECACC under accession number 04090801, wherein the antibody or functional fragment thereof reduces or inhibits the binding of C5a to C5aR.

5. An isolated antibody or a functional fragment thereof that binds to C5aR, wherein the antibody or functional fragment thereof competitively inhibits the binding of a monoclonal antibody as deposited with ECACC under accession number 00110609 to C5aR.

6. An isolated antibody or a functional fragment thereof that binds to C5aR, wherein the antibody or functional fragment thereof competitively inhibits the binding of a monoclonal antibody as deposited with ECACC under accession number 02090226 to C5aR.

7. An isolated antibody or a functional fragment thereof that binds to C5aR, wherein the antibody or functional fragment thereof competitively inhibits the binding of a monoclonal antibody as deposited with ECACC under accession number 04090801 to C5aR.

8. An isolated antibody or a functional fragment thereof according to claim 5, wherein the comparative binding specificity is determined by antibody-antibody competition assays in the presence of C5aR or a polypeptide comprising an extracellular loop of C5aR.

9. An isolated antibody comprising light and heavy chain sequences comprising the amino acid sequences as set forth in SEQ ID NO:19 and SEQ ID NO:21 respectively, or a functional fragment of the antibody, wherein the antibody or functional fragment thereof binds to C5aR and reduces or inhibits the binding of C5a to C5aR.

10. An isolated antibody comprising light and heavy chain sequences comprising the amino acid sequences as set forth in SEQ ID NO:15 and SEQ ID NO:17 respectively, or a functional fragment of the antibody, wherein the antibody or functional fragment thereof binds to C5aR and reduces or inhibits the binding of C5a to C5aR.)

11. An isolated antibody comprising light and heavy chain sequences comprising the amino acid sequences as set forth in SEQ ID NO:23 and SEQ ID NO:25 respectively, or a functional fragment of the antibody, wherein the antibody or functional fragment thereof binds to C5aR and reduces or inhibits the binding of C5a to C5aR.

12. An isolated antibody or a functional fragment thereof according to claim 1, wherein the antibody also inhibits activation of neutrophils by a chemoattractant ligand other than C5a.

13. An isolated antibody according to claim 1, wherein the antibody is a monoclonal or recombinant antibody.

14. An antibody that is reactive with the second extracellular loop of C5aR set forth as the amino acid sequence from residue 175 to 206 of SEQ ID NO: 1, wherein the antibody reduces or inhibits the binding of C5a to C5aR, and wherein the antibody is a chimeric antibody or a humanized antibody.

15. An isolated antibody according to claim 1, wherein the antibody is a class IgG2a or class IgG3 antibody.

16. A monoclonal antibody selected from the group consisting of a monoclonal antibody as deposited with ECACC under accession number 00110609, a monoclonal antibody as deposited with ECACC under accession number 02090226, and a monoclonal antibody as deposited with ECACC under accession number 04090801.

17. A hybridoma as deposited with ECACC under accession number 00110609.

18. A hybridoma as deposited with ECACC under accession number 02090226.

19. A hybridoma as deposited with ECACC under accession number 04090801.

20. A conjugate comprising:
an antibody or a functional fragment thereof that is reactive with the second extracellular loop of C5aR set forth as the amino acid sequence from residue 175 to 206 of SEQ ID NO: 1, wherein the antibody or functional fragment thereof reduces or inhibits the binding of C5a to C5aR; and
a therapeutic agent.

21. A conjugate according to claim 20, wherein the therapeutic agent is a toxin.

22. A conjugate according to claim 20, wherein the toxin is a *Pseudomonas* exotoxin or a derivative thereof.

23. A conjugate comprising:
an antibody or a functional fragment thereof that is reactive with the second extracellular loop of C5aR set forth as the amino acid sequence from residue 175 to 206 of SEQ ID NO: 1, wherein the antibody or functional fragment thereof reduces or inhibits the binding of C5a to C5aR; and
a detectable label.

24. A conjugate according to claim 23, wherein the label is selected from the group consisting of a radiolabel, a fluorescent label, an enzymatic label and contrast media.

25. An isolated nucleic acid molecule, the nucleic acid molecule comprising a sequence encoding the antibody or functional fragment thereof of claim 9.

26. A composition comprising an isolated antibody or a functional fragment thereof according to claim 1 and a pharmaceutically acceptable carrier.

27. A method for inhibiting the interaction of a cell bearing C5aR with a ligand thereof, the method comprising exposing the cell to an isolated antibody or a functional fragment thereof of claim 1.

28. A method for inhibiting C5aR activity in a cell, the method comprising exposing the cell to an isolated antibody or a functional fragment thereof of claim 1.

29. A method for reducing or inhibiting C5a binding to C5aR in a disorder involving neutrophil migration in a subject, the method comprising administering to the subject an isolated antibody or a functional fragment thereof of claim 1.

30. A method for detecting a C5aR in a subject, the method comprising contacting a sample obtained from the subject with a conjugate of claim 23, and detecting immunospecific binding between the conjugate and the sample.

31. A method according to claim 30, wherein the method is performed in vitro using histological specimens or subfractions of tissue or fluid obtained from the subject.

32. A method according to claim 30, wherein the method is performed in vivo.

33. A method for detecting C5aR in a subject, the method comprising administering to the subject an isolated antibody or a functional fragment thereof of claim 1 labeled with an imaging agent under conditions so as to form a complex between the antibody and cells presenting C5aR in the subject, and imaging the complex.

34. A method according to any one of claim 29, wherein the disorder is an immunopathological disorder.

35. A method for delivering a therapeutic agent to a site of inflammation in a subject, the method comprising administering to the subject a conjugate of claim 20.

36. A method for introducing genetic material into cells presenting C5aR, the method comprising contacting the cells with an isolated antibody or a functional fragment thereof of claim 1, wherein the antibody or functional fragment thereof is attached to or associated with genetic material.

37. A method according to claim 36, wherein the cells presenting C5aR are selected from the group consisting of leukocytes, and non-myeloid cells.

38. A method of reducing or inhibiting C5a binding to C5aR in a disorder involving neutrophil migration in a subject, the method comprising introducing into cells of the subject a polynucleotide encoding an isolated antibody or a functional fragment thereof according to claim 1 such that the antibody or functional fragment thereof is expressed in vivo.

39. An isolated antibody comprising:
a heavy chain comprising heavy chain CDR loop sequences CDR1, CDR2 and CDR3 as shown in SEQ ID NO:26, SEQ ID NO:27 and SEQ ID NO:28, respectively; and
a light chain comprising light chain CDR loop sequences as defined by amino acid residues 24 to 39, 55 to 61 and 94 to 102 of the variable light chain sequence as shown in SEQ ID NO:19,
wherein the antibody binds to C5aR and reduces or inhibits the binding of C5a to C5aR.

40. An isolated antibody comprising:
- a heavy chain comprising heavy chain CDR loop sequences CDR1, CDR2 and CDR3 as shown in SEQ ID NO:29, SEQ ID NO:30 and SEQ ID NO:31, respectively; and
- a light chain comprising light chain CDR loop sequences as defined by amino acid residues 24 to 39, 55 to 61 and 94 to 102 of the variable light chain sequence as shown in SEQ ID NO:15,
- wherein the antibody binds to C5aR and reduces or inhibits the binding of C5a to C5aR.

41. An isolated antibody comprising:
- a heavy chain comprising heavy chain CDR loop sequences CDR1, CDR2 and CDR3 as shown in SEQ ID NO:32, SEQ ID NO:33 and SEQ ID NO:34, respectively; and
- a light chain comprising light chain CDR loop sequences as defined by amino acid residues 24 to 39, 55 to 61 and 94 to 102 of the variable light chain sequence as shown in SEQ ID NO:23,
- wherein the antibody binds to C5aR and reduces or inhibits the binding of C5a to C5aR.

42. An isolated antibody comprising a light chain comprising the amino acid sequence as set forth in SEQ ID NO:19, wherein the antibody binds to C5aR and reduces or inhibits the binding of C5a to C5aR.

43. An isolated antibody comprising a heavy chain comprising the amino acid sequence as set forth in SEQ ID NO:21, wherein the antibody binds to C5aR and reduces or inhibits the binding of C5a to C5aR.

44. An isolated antibody comprising a light chain comprising the amino acid sequence as set forth in SEQ ID NO:15, wherein the antibody binds to C5aR and reduces or inhibits the binding of C5a to C5aR.

45. An isolated antibody comprising a heavy chain comprising the amino acid sequence as set forth in SEQ ID NO:17, wherein the antibody binds to C5aR and reduces or inhibits the binding of C5a to C5aR.

46. An isolated antibody comprising a light chain comprising the amino acid sequence as set forth in SEQ ID NO:23, wherein the antibody binds to C5aR and reduces or inhibits the binding of C5a to C5aR.

47. An isolated antibody comprising a heavy chain comprising the amino acid sequence as set forth in SEQ ID NO:25, wherein the antibody binds to C5aR and reduces or inhibits the binding of C5a to C5aR.

48. The isolated antibody or functional fragment thereof according to claim 1, wherein the isolated antibody or functional fragment thereof is a whole antibody.

49. The isolated antibody or functional fragment thereof according to claim 2, wherein the isolated antibody or functional fragment thereof is a whole antibody.

50. The isolated antibody or functional fragment thereof according to claim 3, wherein the isolated antibody or functional fragment thereof is a whole antibody.

51. The isolated antibody or functional fragment thereof according to claim 4, wherein the isolated antibody or functional fragment thereof is a whole antibody.

52. The isolated antibody or functional fragment thereof according to claim 5, wherein the isolated antibody or functional fragment thereof is a whole antibody.

53. The isolated antibody or functional fragment thereof according to claim 6, wherein the isolated antibody or functional fragment thereof is a whole antibody.

54. The isolated antibody or functional fragment thereof according to claim 7, wherein the isolated antibody or functional fragment thereof is a whole antibody.

55. The isolated antibody or functional fragment thereof according to claim 8, wherein the isolated antibody or functional fragment thereof is a whole antibody.

56. The conjugate according to claim 20, wherein the antibody or functional fragment thereof is a whole antibody.

57. The conjugate according to claim 23, wherein the antibody or functional fragment thereof is a whole antibody.

58. The method according to claim 33, wherein the isolated antibody or functional fragment thereof is a whole antibody.

59. The method according to claim 36, wherein the isolated antibody or functional fragment thereof is a whole antibody.

60. The method according to claim 38, wherein the isolated antibody or functional fragment thereof is a whole antibody.

61. An isolated antibody or a functional fragment thereof according to claim 6, wherein the competitive binding specificity is determined by antibody-antibody competition assays in the presence of C5aR or a polypeptide comprising an extracellular loop of C5aR.

62. An isolated antibody or a functional fragment thereof according to claim 7, wherein the competitive binding specificity is determined by antibody-antibody competition assays in the presence of C5aR or a polypeptide comprising an extracellular loop of C5aR.

63. A method according to claim 36, wherein the cells presenting C5aR are selected from the group consisting of granulocytes, monocytes, macrophages, basophils, eosinophils, mast cells and lymphocytes.

64. A method according to claim 36, wherein the cells presenting C5aR are selected from the group consisting of T cells and dendritic cells.

65. A method according to claim 36, wherein the cells presenting C5aR are selected from the group consisting of endothelial cells and smooth muscle cells.

66. An isolated nucleic acid molecule, the nucleic acid molecule comprising a sequence encoding the antibody or functional fragment thereof of claim 10.

67. An isolated nucleic acid molecule, the nucleic acid molecule comprising a sequence encoding the antibody or functional fragment thereof of claim 11.

* * * * *

SEQUENCE LISTING

<160> NUMBER OF SEQ ID NOS: 34

<210> SEQ ID NO 1
<211> LENGTH: 350
<212> TYPE: PRT
<213> ORGANISM: Homo sapiens

<400> SEQUENCE: 1

Met Asn Ser Phe Asn Tyr Thr Thr Pro Asp Tyr Gly His Tyr Asp Asp
1               5                   10                  15

Lys Asp Thr Leu Asp Leu Asn Thr Pro Val Asp Lys Thr Ser Asn Thr
            20                  25                  30

-continued

Leu Arg Val Pro Asp Ile Leu Ala Leu Val Ile Phe Ala Val Phe
            35                  40                  45

Leu Val Gly Val Leu Gly Asn Ala Leu Val Val Trp Val Thr Ala Phe
 50                  55                  60

Glu Ala Lys Arg Thr Ile Asn Ala Ile Trp Phe Leu Asn Leu Ala Val
 65                  70                  75                  80

Ala Asp Phe Leu Ser Cys Leu Ala Leu Pro Ile Leu Phe Thr Ser Ile
                85                  90                  95

Val Gln His His His Trp Pro Phe Gly Gly Ala Ala Cys Ser Ile Leu
                100                 105                 110

Pro Ser Leu Ile Leu Leu Asn Met Tyr Ala Ser Ile Leu Leu Leu Ala
            115                 120                 125

Thr Ile Ser Ala Asp Arg Phe Leu Leu Val Phe Lys Pro Ile Trp Cys
            130                 135                 140

Gln Asn Phe Arg Gly Ala Gly Leu Ala Trp Ile Ala Cys Ala Val Ala
145                 150                 155                 160

Trp Gly Leu Ala Leu Leu Leu Thr Ile Pro Ser Phe Leu Tyr Arg Val
                165                 170                 175

Val Arg Glu Glu Tyr Phe Pro Pro Lys Val Leu Cys Gly Val Asp Tyr
            180                 185                 190

Ser His Asp Lys Arg Arg Glu Arg Ala Val Ala Ile Val Arg Leu Val
            195                 200                 205

Leu Gly Phe Leu Trp Pro Leu Leu Thr Leu Thr Ile Cys Tyr Thr Phe
            210                 215                 220

Ile Leu Leu Arg Thr Trp Ser Arg Arg Ala Thr Arg Ser Thr Lys Thr
225                 230                 235                 240

Leu Lys Val Val Val Ala Val Val Ala Ser Phe Phe Ile Phe Trp Leu
                245                 250                 255

Pro Tyr Gln Val Thr Gly Ile Met Met Ser Phe Leu Glu Pro Ser Ser
            260                 265                 270

Pro Thr Phe Leu Leu Leu Asn Lys Leu Asp Ser Leu Cys Val Ser Phe
            275                 280                 285

Ala Tyr Ile Asn Cys Cys Ile Asn Pro Ile Ile Tyr Val Val Ala Gly
            290                 295                 300

Gln Gly Phe Gln Gly Arg Leu Arg Lys Ser Leu Pro Ser Leu Leu Arg
305                 310                 315                 320

Asn Val Leu Thr Glu Glu Ser Val Val Arg Glu Ser Lys Ser Phe Thr
                325                 330                 335

Arg Ser Thr Val Asp Thr Met Ala Gln Lys Thr Gln Ala Val
            340                 345                 350

<210> SEQ ID NO 2
<211> LENGTH: 23
<212> TYPE: DNA
<213> ORGANISM: Artificial Sequence
<220> FEATURE:
<223> OTHER INFORMATION: PCR primer

<400> SEQUENCE: 2
gatgttttga tgacccaaac tcc                                          23

<210> SEQ ID NO 3
<211> LENGTH: 25
<212> TYPE: DNA
<213> ORGANISM: Artificial Sequence
<220> FEATURE:
<223> OTHER INFORMATION: PCR primer

```
<400> SEQUENCE: 3
acactcattc ctgttgaagc tcttg                                              25

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
saggtccagc tgcarcagtc                                                    20

<210> SEQ ID NO 5
<211> LENGTH: 18
<212> TYPE: DNA
<213> ORGANISM: Artificial Sequence
<220> FEATURE:
<223> OTHER INFORMATION: PCR primer

<400> SEQUENCE: 5
tgggcatgaa gaacctgg                                                      18

<210> SEQ ID NO 6
<211> LENGTH: 23
<212> TYPE: DNA
<213> ORGANISM: Artificial Sequence
<220> FEATURE:
<223> OTHER INFORMATION: PCR primer

<400> SEQUENCE: 6
gatgttttga tgacccaaac tcc                                                23

<210> SEQ ID NO 7
<211> LENGTH: 25
<212> TYPE: DNA
<213> ORGANISM: Artificial Sequence
<220> FEATURE:
<223> OTHER INFORMATION: PCR primer

<400> SEQUENCE: 7
acactcattc ctgttgaagc tcttg                                              25

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
saggtccagc tgcarcagtc                                                    20

<210> SEQ ID NO 9
<211> LENGTH: 18
<212> TYPE: DNA
<213> ORGANISM: Artificial Sequence
<220> FEATURE:
<223> OTHER INFORMATION: PCR primer

<400> SEQUENCE: 9
tttgcatgga ggacaggg                                                      18

<210> SEQ ID NO 10
<211> LENGTH: 23
```

<212> TYPE: DNA
<213> ORGANISM: Artificial Sequence
<220> FEATURE:
<223> OTHER INFORMATION: PCR primer

<400> SEQUENCE: 10
gatgttttga tgacccaaac tcc                                          23

<210> SEQ ID NO 11
<211> LENGTH: 25
<212> TYPE: DNA
<213> ORGANISM: Artificial Sequence
<220> FEATURE:
<223> OTHER INFORMATION: PCR primer

<400> SEQUENCE: 11
acactcattc ctgttgaagc tcttg                                        25

<210> SEQ ID NO 12
<211> LENGTH: 20
<212> TYPE: DNA
<213> ORGANISM: Artificial Sequence
<220> FEATURE:
<223> OTHER INFORMATION: PCR primer

<400> SEQUENCE: 12
caggtgcagc tgaagsagtc                                              20

<210> SEQ ID NO 13
<211> LENGTH: 18
<212> TYPE: DNA
<213> ORGANISM: Artificial Sequence
<220> FEATURE:
<223> OTHER INFORMATION: PCR primer

<400> SEQUENCE: 13
tgggcatgaa gaacctgg                                                18

<210> SEQ ID NO 14
<211> LENGTH: 336
<212> TYPE: DNA
<213> ORGANISM: Mus musculus

<400> SEQUENCE: 14
gatgttgtga tgacccaaat tccactctcc ctgcctgtca gtcttggaga tcaaacctcc    60
atctcttgca gatctagtca gagccttata cacagtaatg gaaacaccta tttacattgg   120
tacctgcaga agccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tatgggagtt tatttctgct ctcaaagtac acatgttcct   300
ccgacgttcg gtggaggcac caagctggaa atcaaa                            336

<210> SEQ ID NO 15
<211> LENGTH: 112
<212> TYPE: PRT
<213> ORGANISM: Mus musculus

<400> SEQUENCE: 15

Asp Val Val Met Thr Gln Ile Pro Leu Ser Leu Pro Val Ser Leu Gly
1               5                   10                  15

Asp Gln Thr Ser Ile Ser Cys Arg Ser Ser Gln Ser Leu Ile His Ser
            20                  25                  30

Asn Gly Asn Thr Tyr Leu His Trp Tyr Leu Gln Lys Pro Gly Gln Ser

```
                 35                  40                  45
Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Met Gly Val Tyr Phe Cys Ser Gln Ser
                 85                  90                  95

Thr His Val Pro Pro Thr Phe Gly Gly Gly Thr Lys Leu Glu Ile Lys
                100                 105                 110

<210> SEQ ID NO 16
<211> LENGTH: 363
<212> TYPE: DNA
<213> ORGANISM: Mus musculus

<400> SEQUENCE: 16
caggttcagc tgcagcagtc tggacctgag gtggtgaagc ctggggcctc agtgaagatt      60
tcctgcaagg cttctggcta cgcattcagt aggtcctgga tgaactgggt gaagcagagg     120
cctggaaagg gtcttgagtg gattggacgg attgatgctg gagatggaga tactaaatac     180
aatgggaagt tcaagggcaa ggccacactg actgcagaca atcctccag cacagcctac      240 atgcaactca gcagcctgac atctgaggac tctgcggtct acttctgtgc aagccttctc     300
attactacgg tagtgggagc tatggactac tggggtcaag aacctcagt caccgtctcc      360 tca                                                                    363

<210> SEQ ID NO 17
<211> LENGTH: 121
<212> TYPE: PRT
<213> ORGANISM: Mus musculus

<400> SEQUENCE: 17

Gln Val Gln Leu Gln Gln Ser Gly Pro Glu Val Val Lys Pro Gly Ala
 1               5                  10                  15

Ser Val Lys Ile Ser Cys Lys Ala Ser Gly Tyr Ala Phe Ser Arg Ser
                 20                  25                  30

Trp Met Asn Trp Val Lys Gln Arg Pro Gly Lys Gly Leu Glu Trp Ile
             35                  40                  45

Gly Arg Ile Asp Ala Gly Asp Gly Asp Thr Lys Tyr Asn Gly Lys Phe
         50                  55                  60

Lys Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Ser Leu Leu Ile Thr Thr Val Val Gly Ala Met Asp Tyr Trp Gly
                100                 105                 110

Gln Gly Thr Ser Val Thr Val Ser Ser
            115                 120

<210> SEQ ID NO 18
<211> LENGTH: 336
<212> TYPE: DNA
<213> ORGANISM: Mus musculus

<400> SEQUENCE: 18
gatgttgtga tgacccaatc tccactctcc ctgcctgtca gtcttggaaa tcaagcctcc      60
atctcttgca gatctagtca gagccttgta cacagtaatg gaaacaccta tttacattgg    120
```

```
tacctgcaga agccaggcca gtctccaaag ctcctgatct acaaagtttc caaccgattt      180
tctggggtcc cagacaggtt cagtggcagt ggatcaggga cagatttctc actcaagatc      240
agcagagtgg aggctgagga tctgggagtt tatttctgct ctcaaagtac acttgttccg      300
ctcacgttcg gtgctgggac caagctggaa ctgaaa                               336
```

<210> SEQ ID NO 19
<211> LENGTH: 112
<212> TYPE: PRT
<213> ORGANISM: Mus musculus

<400> SEQUENCE: 19

```
Asp Val Val Met Thr Gln Ser Pro Leu Ser Leu Pro Val Ser Leu Gly
1               5                  10                  15

Asn Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Ser Leu Lys Ile
65                  70                  75                  80

Ser Arg Val Glu Ala Glu Asp Leu Gly Val Tyr Phe Cys Ser Gln Ser
                85                  90                  95

Thr Leu Val Pro Leu Thr Phe Gly Ala Gly Thr Lys Leu Glu Leu Lys
            100                 105                 110
```

<210> SEQ ID NO 20
<211> LENGTH: 363
<212> TYPE: DNA
<213> ORGANISM: Mus musculus

<400> SEQUENCE: 20

```
caggttcagc tgcagcagtc tggacctgag ctggtgaagc ctggggcctc agtgaagatt       60
tcctgcaagg cttctggcta cgcattcagt aactcctgga tgaactgggt gaagcagagg      120
cctggaaagg gtcttgagtg gattggacgg atttatcctg agatggaga tactaagtac       180 aatgggaagt tcaagggcaa ggccacactg actgcagaca atcctccag cacagcctac       240 atgcaactca gcagcctgac atctgaggac tctgcggtct atttctgtgc aagattccta      300
cttattagta cggtaacagc cgttgactac tggggccaag gcaccactct cacagtctcc      360
tca                                                                   363
```

<210> SEQ ID NO 21
<211> LENGTH: 121
<212> TYPE: PRT
<213> ORGANISM: Mus musculus

<400> SEQUENCE: 21

```
Gln Val Gln Leu Gln Gln Ser Gly Pro Glu Leu Val Lys Pro Gly Ala
1               5                  10                  15

Ser Val Lys Ile Ser Cys Lys Ala Ser Gly Tyr Ala Phe Ser Asn Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Asp Thr Lys Tyr Asn Gly Lys Phe
    50                  55                  60

Lys Gly Lys Ala Thr Leu Thr Ala Asp Lys Ser Ser Ser Thr Ala Tyr
```

```
                65                  70                  75                  80
Met Gln Leu Ser Ser Leu Thr Ser Glu Asp Ser Ala Val Tyr Phe Cys
                        85                  90                  95

Ala Arg Phe Leu Leu Ile Ser Thr Val Thr Ala Val Asp Tyr Trp Gly
                100                 105                 110

Gln Gly Thr Thr Leu Thr Val Ser Ser
            115                 120
```

<210> SEQ ID NO 22
<211> LENGTH: 336
<212> TYPE: DNA
<213> ORGANISM: Mus musculus

<400> SEQUENCE: 22

```
gatgttgtga tgacccaaac tccactctcc ctgcctgtca gtcttggaga tcaagcctcc      60
atctcttgta gatctagtca gagccttgta cacagtagtg aaacaccta  tttacattgg    120
tacctgcaga agccaggcca gtctccaaag ctcctgatct acaaagtctc caaccgattt    180
tctggggtcc cagacaggtt cagtggcagt ggatcaggga cacatttcac actcaagatc    240
agcagagtgg aggctgagga tctgggaatt tatttctgct ctcaaagtac acttgttcct    300
ccgacgttcg gtggaggcac caagctggaa atcaaa                              336
```

<210> SEQ ID NO 23
<211> LENGTH: 112
<212> TYPE: PRT
<213> ORGANISM: Mus musculus

<400> SEQUENCE: 23

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Ser Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr His Phe Thr Leu Lys Ile
65                  70                  75                  80

Ser Arg Val Glu Ala Glu Asp Leu Gly Ile Tyr Phe Cys Ser Gln Ser
                85                  90                  95

Thr Leu Val Pro Pro Thr Phe Gly Gly Gly Thr Lys Leu Glu Ile Lys
            100                 105                 110
```

<210> SEQ ID NO 24
<211> LENGTH: 357
<212> TYPE: DNA
<213> ORGANISM: Mus musculus

<400> SEQUENCE: 24

```
caggtgcagc tgaaggagtc aggacctggc ctggtggcgc cctcacagag cctgtccatc      60
acatgcactg tctctgggtt ctcattaacc agctatggtg tagactgggt tcgccagtct    120
ccaggaaagg gtctggagtg gctgggagta atatgggggt tggaagcac  aaattataat    180
tcagctctca aatccagact gagcatcagc aaggacaact ccaagagcca gttttcttta    240
aaaatgaaca gtctgcaaac tgatgacgca gccatgtact actgtgccag ccactatggt    300
tacgacggtc tggggtttgc ttactggggc caagggactc tggtcactgt ctctgta       357
```

```
<210> SEQ ID NO 25
<211> LENGTH: 119
<212> TYPE: PRT
<213> ORGANISM: Mus musculus

<400> SEQUENCE: 25

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Asp Trp Val Arg Gln Ser Pro Gly Lys Gly Leu Glu Trp Leu
        35                  40                  45

Gly Val Ile Trp Gly Val Gly Ser Thr Asn Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Ala Ala Met Tyr Tyr Cys Ala
                85                  90                  95

Ser His Tyr Gly Tyr Asp Gly Leu Gly Phe Ala Tyr Trp Gly Gln Gly
            100                 105                 110

Thr Leu Val Thr Val Ser Val
        115

<210> SEQ ID NO 26
<211> LENGTH: 5
<212> TYPE: PRT
<213> ORGANISM: Mus musculus

<400> SEQUENCE: 26

Asn Ser Trp Asn Asn
1               5

<210> SEQ ID NO 27
<211> LENGTH: 17
<212> TYPE: PRT
<213> ORGANISM: Mus musculus

<400> SEQUENCE: 27

Arg Ile Tyr Pro Gly Asp Gly Asp Thr Lys Tyr Asn Gly Lys Phe Lys
1               5                   10                  15

Gly

<210> SEQ ID NO 28
<211> LENGTH: 12
<212> TYPE: PRT
<213> ORGANISM: Mus musculus

<400> SEQUENCE: 28

Phe Leu Leu Ile Ser Thr Val Thr Ala Val Asp Tyr
1               5                   10

<210> SEQ ID NO 29
<211> LENGTH: 5
<212> TYPE: PRT
<213> ORGANISM: Mus musculus

<400> SEQUENCE: 29

Arg Ser Trp Met Asn
1               5

<210> SEQ ID NO 30
```

-continued

```
<211> LENGTH: 17
<212> TYPE: PRT
<213> ORGANISM: Mus musculus

<400> SEQUENCE: 30

Arg Ile Asp Ala Gly Asp Gly Asp Thr Lys Tyr Asn Gly Lys Phe Lys
1               5                   10                  15
Gly

<210> SEQ ID NO 31
<211> LENGTH: 12
<212> TYPE: PRT
<213> ORGANISM: Mus musculus

<400> SEQUENCE: 31

Leu Leu Ile Thr Thr Val Val Gly Ala Met Asp Tyr
1               5                   10

<210> SEQ ID NO 32
<211> LENGTH: 5
<212> TYPE: PRT
<213> ORGANISM: Mus musculus

<400> SEQUENCE: 32

Ser Tyr Gly Val Asp
1               5

<210> SEQ ID NO 33
<211> LENGTH: 16
<212> TYPE: PRT
<213> ORGANISM: Mus musculus

<400> SEQUENCE: 33

Val Ile Trp Gly Val Gly Ser Thr Asn Tyr Asn Ser Ala Leu Lys Ser
1               5                   10                  15

<210> SEQ ID NO 34
<211> LENGTH: 11
<212> TYPE: PRT
<213> ORGANISM: Mus musculus

<400> SEQUENCE: 34

His Tyr Gly Tyr Asp Gly Leu Gly Phe Ala Tyr
1               5                   10
```